(12) United States Patent
Ina et al.

(10) Patent No.: US 6,265,402 B1
(45) Date of Patent: Jul. 24, 2001

(54) USE OF 2-PHENYLMORPHOLIN-5-ONE DERIVATIVES

(75) Inventors: Shinji Ina; Kenjirou Yamana; Kyoji Noda, all of Omiya (JP)

(73) Assignee: Nikken Chemicals Co., Ltd., Tokyo (JP)

( * ) Notice: Subject to any disclaimer, the term of this patent is extended or adjusted under 35 U.S.C. 154(b) by 0 days.

(21) Appl. No.: 09/242,818

(22) PCT Filed: Aug. 26, 1997

(86) PCT No.: PCT/JP97/02970

§ 371 Date: Feb. 25, 1999

§ 102(e) Date: Feb. 25, 1999

(87) PCT Pub. No.: WO98/08828

PCT Pub. Date: Mar. 5, 1998

(30) Foreign Application Priority Data

Aug. 27, 1996 (JP) .................................................. 8-242542

(51) Int. Cl.$^7$ ....................... A61K 31/5375; A61P 19/02; C07D 265/32
(52) U.S. Cl. ........................ 514/230.8; 544/128; 544/131; 544/174
(58) Field of Search ................................... 544/174, 131; 514/230.8

(56) References Cited

U.S. PATENT DOCUMENTS 3,308,121 * 3/1967 Gannon et al. ................ 544/174
5,128,358   7/1992 Saccomano et al. .

FOREIGN PATENT DOCUMENTS

| 50-157360 | 12/1975 | (JP) . |
| 59-116288 | 7/1984 | (JP) . |
| 62-281864 | 12/1987 | (JP) . |
| 64-6262 | 1/1989 | (JP) . |
| 3209322 | 9/1991 | (JP) . |
| 5-117239 | 5/1993 | (JP) . |
| 7-101861 | 4/1995 | (JP) . |
| 8501318 | 2/1996 | (JP) . |
| WO94/10118 | 5/1994 | (WO) . |
| WO94/12461 | 6/1994 | (WO) . |
| WO95/03794 | 2/1995 | (WO) . |
| WO95/08534 | 9/1995 | (WO) . |

OTHER PUBLICATIONS

P.J. Barnes, et al., "Theophylline in the management of asthma: time for reappraisal?" Eur. Respir. J., vol. 7, pp. 579–591.

C. David Nicholson, et al., "Differential modulation of tissue function and therapeutic potential of selective inhibitors of cyclic nucleotide phosphodiesterase isoenzymes" TIPS, Jan., 1991 [vol. 12], pp. 19–27.

T. J. Torphy, et al., "Phosphodiesterase inhibitors: new opportunities for the treatment of asthma", Thorax 1991; vol. 46, pp. 512–523.

D. C. Underwood, et al., "Inhibition of Antigen–Induced Bronchoconstriction and Eosinophil Infiltration in the Guinea Pig by the Cyclic AMP–Specific Phosphodiesterase Inhibitor, Rolipram", The Journal of Pharmacology and Experimental Therapeutics, vol. 266, No. 1, pp. 306–313.

M.M. Teixeira, et al., "Effects of phosphodiesterase isoenzyme inhibitors on cutaneous inflammation in the guine-a–pig", Br. J. Pharmacol. (1994) vol. 112, pp. 332–340.

N. Sommer, et al., "The antidepressant rolipram suppreses cytokine production and prevents autoimmune encephalo-myelitis" Nature Medicine, vol. 1, No. 3, Mar., 1995, pp. 244–248.

L. Sekut, et al., "Anti–inflammatory activity of phosphodi-esterase (PDE)–IV inhibitors in acute and chronic models of inflammation", Clin. Exp. Immunol. 1995, vol. 100; pp. 126–132.

D.A. Evans, et al., "Cyanosilylation of Aldehydes and Ketones. A Convenient Route to Cyanohydrin Derivatives", J.C.S. Chem. Comm. 1973, pp. 55–56.

W. E. Parham, et al., "A New Synthesis of β–Amino Alcohols", Tetrahedron Letters No. 14, pp. 923–926 (1971).

* cited by examiner

Primary Examiner—Robert W. Ramsuer
(74) Attorney, Agent, or Firm—Christie, Parker & Hale, LLP

(57) ABSTRACT

A 2-phenylmorpholin-5-one derivative having the formula (I):

(I)

wherein $R_1$ represents a $C_1$ to $C_8$ alkyl group, a $C_3$ to $C_7$ cycloalkyl group or an indanyl group, $R_2$ represents a $C_1$ to $C_4$ alkyl group, $R_3$ represents a hydrogen atom, a $C_1$ to $C_5$ alkyl group, etc., $R_4$ represents a hydrogen atom, a $C_1$ to $C_6$ alkyl group, etc., $R_5$, $R_6$ represent a hydrogen atom, a $C_1$ to $C_5$ alkyl group, etc., an optical isomer thereof or a pharmacologically acceptable salt thereof, or a hydrate or solvate thereof and a pharmaceutical composition containing the same.

The above compound has a strong type IV phosphodi-esterase (PDE) inhibitory activity and has bronchodilater and antiinflammatory effects.

14 Claims, No Drawings

USE OF 2-PHENYLMORPHOLIN-5-ONE DERIVATIVES

This application is a 371 of PCT/JP97/02970 filed Aug. 26, 1997.

TECHNICAL FIELD

The present invention relates to a novel 2-phenylmorpholin-5-one derivative having a type IV phosphodiesterase (PDE) inhibitory activity and a pharmaceutical composition containing the same.

BACKGROUND ART

Intracellular second messenger cAMP is involved in relaxation of airway smooth muscles and regulation of the functions of inflammatory cells. cAMP is broken down by phosphodiesterase (PDE) and becomes inactive 5'-AMP. It is considered that an increase in concentration of cAMP due to suppression of cAMP metabolism by PDE would give bronchodilating and anti-inflammatory actions and would exhibit a therapeutic effect on inflammatory diseases such as asthma [Eur. Respir. J., 7, 579 (1994)]. Up to now, PDE has been classified into five isozymes (i.e., types I to V PDE). Their distributions differ among tissues [Trends Pharm., Sci., 12, 19 (1991)]. This suggests a possibility that selective inhibitors of PDE isozymes would result in tissue specific increase of intracellular cAMP concentration.

It is reported that a selective inhibitor of type IV PDE isozyme suppresses inflammatory cells functions [Thorax, 46, 512 (1991)] and is useful for inflammatory diseases such as asthma [J. Pharmacol. Exp. Ther., 266, 306 (1993)] and dermatitis [Br. J. Pharmacol., 112, 332 (1994)] and autoimmune diseases such as multiple sclerosis [Nature Medicine, 1, 244 (1994)] and rheumatoid arthritis [Clin. Exp. Immunol., 100, 126 (1995)].

In addition, it is thought that cardiovascular side effect caused by non-selective PDE inhibitors such as theophylline could be reduced by using selective type IV PDE inhibitor. Rolipram having the following formula (Japanese Unexamined Patent Publication (Kokai) No. 50-157360) is known as a compound having a specific inhibitory activity against type IV PDE.

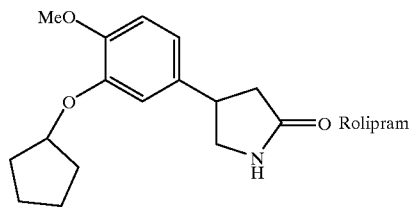
Rolipram

Although other compounds having a specific inhibitory activity against type IV PDE are known (Japanese Unexamined Patent Publication (Kokai) No. 62-281864, U.S. Pat. No. 5,128,358, WO 94/10118, WO 94/12461, Japanese Unexamined Patent Publication (Kokai) No. 5-117239, Japanese Unexamined Patent Publication (Kokai) No. 7-101861, WO 95/03794, WO 95/08534, etc.), they have not been clinically applied up to now. Thus, more useful compounds are desired to be. Further, Japanese Unexamined Patent Publication (Kokai) No. 64-6262 discloses a compound having the following formula (II)

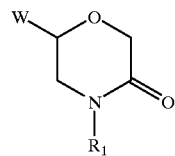

wherein W is optionally substituted phenyl group, and RI is secondary or tertiary $C_3$ to $C_6$ alkyl group as a synthetic intermediate of a compound having the activity of increasing the weight gain of livestock and/or improving feed utilization efficiency. Japanese Unexamined Patent Publication (Kokai) No. 59-116288 describes a compound having the following formula (III):

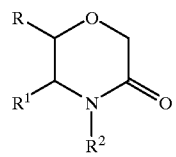

wherein R and $R_1$ may be the same or different and represent a hydrogen atom, a $C_1$ to $C_{18}$ alkyl group or a phenyl group, which groups may be substituted, $R_2$ represents a hydrogen atom, a $C_1$ to $C_6$ alkyl group, a $C_8$ to $C_{18}$ arylalkyl group which may be substituted with any number up to five of fluorine atoms, chlorine atoms, or bromine atoms, etc.

as a synthetic intermediate of a compound having a lipoxygenase inhibitory activity. U.S. Pat. No. 3,308,121 describes a compound having the following formula (IV):

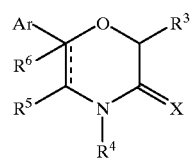

wherein $R_3$ represents a hydrogen atom or a lower hydroxyalkyl group, $R_4$ represents a hydrogen atom, a lower alkyl group, an acyl group, etc., $R_5$ and $R_6$ independently represent a hydrogen atom, a lower alkyl group or an aryl group, Ar represents a phenyl group and a substituted phenyl group substituted with a halogen atom, a hydroxy group, a lower alkoxy group, a benzyloxy or a halogenated lower alkyl group, and X indicates an oxygen atom or a sulfur atom, as a muscle relaxant and tranquillizer.

DISCLOSURE OF THE INVENTION

An object of the present invention is to develop a novel compound having a type IV PDE inhibitory activity.

In accordance with the present invention, there are provided a 2-phenylmorpholin-5-one derivative having the formula (I):

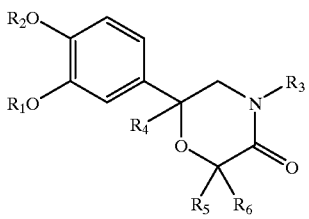

(I)

wherein $R_1$ represents a substituted or unsubstituted $C_1$ to $C_8$ alkyl group; a substituted or unsubstituted $C_3$ to $C_7$ cycloalkyl group; or indanyl group, $R_2$ represents a $C_1$ to $C_4$ alkyl group, $R_3$ represents a hydrogen atom; a substituted or unsubstituted $C_1$ to $C_5$ alkyl group; a substituted or unsubstituted $C_3$ to $C_7$ cycloalkyl group; a substituted or unsubstituted aryl group which may include at least one hetero atom selected from the group consisting of an oxygen atom, a nitrogen atom and a sulfur atom; or an acyl group, $R_4$ represents a hydrogen atom; a substituted or unsubstituted $C_1$ to $C_6$ alkyl group; or a substituted or unsubstituted aryl group which may include at least one hetero atom selected from the group consisting of an oxygen atom, a nitrogen atom and a sulfur atom, $R_5$ and $R_6$ independently represents a hydrogen atom; a substituted or unsubstituted $C_1$ to $C_5$ alkyl group; a substituted or unsubstituted $C_3$ to $C_7$ cycloalkyl group; or a substituted or unsubstituted aryl group which may include at least one hetero atom selected from the group consisting of an oxygen atom, a nitrogen atom and a sulfur atom, an optical isomer thereof, or a pharmacologically acceptable salt thereof, or a hydrate or solvate thereof; and a pharmaceutical composition comprising, as an essential ingredient, these compounds.

BEST MODE FOR CARRYING OUT THE INVENTION

The present invention will be explained in detail below.

The present inventors conducted a search for a novel compound having a type IV PDE inhibitory activity and, as a result, found that the above 2-phenylmorpholin-5-one derivative had a strong type IV PDE inhibitory activity and had a bronchodilator and antiinflammatory effects, whereby the present invention was completed.

As the $C_1$ to $C_8$ linear or branched alkyl group of $R_1$ in the compound having the above formula (I), methyl, ethyl, propyl, isopropyl, n-butyl, 2-methylpropyl, sec-butyl, t-butyl, n-pentyl, 1,1-dimethylpropyl, n-hexyl, 1-methylpentyl, 1,1-dimethylbutyl, 2-ethylbutyl, n-heptyl, n-octyl, etc. may be mentioned. These groups may be substituted with a halogen atom; a hydroxy group; a nitro group; a cyano group; an amino group; a carboxyl group; an aryl group such as phenyl, tolyl, naphthyl, pyridyl, thiazolyl, thienyl, furyl, quinolyl, etc.; a cycloalkyl group such as cyclopropyl, cyclobutyl, cyclopentyl, cyclohexyl, etc.; a haloalkyl group; a carbamoyl group; an alkoxy group; an alkylcarbonyl group; etc. Specifically, as the substituents for the substituted $C_1$ to $C_8$ alkyl group, cyclopropylmethyl, cyclobutylmethyl, cyclopentylmethyl, cyclohexylmethyl, 1-methylcyclopropylmethyl, 1-phenylcyclopropylmethyl, 1-methylcyclobutylmethyl, 1-methylcyclopentylmethyl, 1-methylcyclohexylmethyl, 2-indanylmethyl, benzyl, phenethyl, 4-fluorophenethyl, 3-phenylpropyl, 4-phenylbutyl, 5-phenylpentyl, 2-(1-naphthyl)ethyl, 2-(2-pyridyl)ethyl, 2-(benzyloxy)ethyl, 2-(phenethyloxy)ethyl, 2-(methoxy)ethyl, 3-(methoxy)propyl, 4-(methoxy)butyl, 2-(cyclopropylmethoxy)ethyl, 2-(cyclopentyloxy)ethyl, 2-(2-indanyl)ethyl, etc. may be mentioned.

As the $C_3$ to $C_7$ cycloalkyl group of $R_1$, cyclopropyl, cyclobutyl, cyclopentyl, cyclohexyl, cycloheptyl, etc. may be mentioned. These groups may be substituted with a halogen atom; an alkyl group; a hydroxy group; a nitro group; a cyano group; an amino group; a carboxyl group; an aryl group such as phenyl, tolyl, naphthyl, pyridyl, thiazolyl, thienyl, furyl, quinolyl, etc.; a cycloalkyl group such as cyclopropyl, cyclobutyl, cyclopentyl, cyclohexyl, etc.; a haloalkyl group; a carbamoyl group; an alkoxyl group; an alkylcarbonyl group; etc. Specifically, as the substituents for the substituted $C_3$ to $C_7$ cycloalkyl group, 4-phenylcyclohexyl, 1-methylcyclopentyl, etc. may be mentioned. Further, as the substituent $R_1$, an indanyl group may be mentioned.

As the substituent $R_1$, preferably, a $C_1$ to $C_6$ alkyl group; a substituted $C_1$ to $C_5$ alkyl group substituted with at least one group selected from the group consisting of a substituted or unsubstituted aryl group, a substituted or unsubstituted alkoxy group, and a substituted or unsubstituted $C_3$ to $C_7$ cycloalkyl group; a substituted or unsubstituted $C_4$ to $C_6$ cycloalkyl group; or an indanyl group may be mentioned, more preferably methyl; n-butyl; 2-methylpropyl; cyclopropylmethyl; cyclobutylmethyl; cyclopentylmethyl; a $C_1$ to $C_5$ alkyl group substituted with phenyl, naphthyl, benzyloxy, 4-fluorophenyl, phenylcyclopropyl, methylcyclopropyl, or indanyl; cyclopentyl; cyclohexyl; 4-phenylcyclohexyl; or 2-indanyl may be mentioned.

As the $C_1$ to $C_4$ linear or branched alkyl group of $R_2$, methyl, ethyl, n-propyl, isopropyl, n-butyl, sec-butyl, t-butyl, etc. may be mentioned. Preferably, methyl or ethyl may be mentioned. More preferably, methyl may be mentioned.

As $R_3$, a hydrogen atom may be mentioned. Further, as the $C_1$ to $C_5$ linear or branched alkyl group of $R_3$, methyl, ethyl, n-propyl, isopropyl, n-butyl, sec-butyl, t-butyl, n-pentyl, etc. may be mentioned. The $C_1$ to $C_5$ linear or branched alkyl group may be substituted with a halogen atom; a hydroxy group; a nitro group; a cyano group; an amino group; a carbonyl group; an aryl group which may include at least one hetero atom selected from an oxygen atom, a nitrogen atom and a sulfur atom (e.g., phenyl, tolyl, naphthyl, pyridyl, thiazolyl, furyl, thienyl); or alkoxycarbonyl group. Specifically, as the substituents for the substituted $C_1$ to $C_5$ alkyl group, ethoxycarbonylmethyl, benzyl, 4-bromobenzyl, phenethyl, 3-phenylpropyl, 4-phenylbutyl, 5-phenylpentyl, pyridylmethyl, furylmethyl, thiazolylmethyl, 2-quinolylemethyl, 1-naphthylmethyl, 2-naphthylmethyl, etc. may be mentioned.

Further, as the $C_3$ to $C_7$ cycloalkyl group of $R_3$, cyclopropyl, cyclobutyl, cyclopentyl, cyclohexyl, cycloheptyl, etc. may be mentioned. As the aryl group of $R_3$ which may include at least one hetero atom selected from an oxygen atom, a nitrogen atom and a sulfur atom, phenyl, tolyl, naphthyl, pyridyl, thiazolyl, furyl, thienyl, etc. may be mentioned, and as the acyl group of $R_3$, formyl, acetyl, propionyl, benzoyl, 2-naphthoyl, 3-furoyl, 2-thenoyl, nicotinoyl, isonicotinoyl, etc. may be mentioned.

As the substituent $R_3$, preferably, a hydrogen atom; a $C_1$ to $C_4$ alkyl group; a $C_1$ to $C_3$ alkyl group substituted with an aryl group which may be substituted with a halogen atom and may include at least one hetero atom selected from an oxygen atom, a nitrogen atom and a sulfur atom or with an ethoxycarbonyl group; or an acetyl group may be mentioned. More preferably a hydrogen atom, methyl, ethyl, benzyl, 2-pyridylmethyl or 4-pyridylmethyl may be mentioned.

As the substituent $R_4$, a hydrogen atom may be mentioned. As the $C_1$ to $C_6$ linear or branched alkyl group of $R_4$, methyl, ethyl, propyl, isopropyl, butyl, sec-butyl, t-butyl, pentyl, hexyl, etc. may be mentioned, and as the substituted or unsubstituted aryl group of $R_4$, phenyl, 4-methylphenyl, 4-chlorophenyl, pyridyl, thiazolyl, thienyl, furyl, etc. may be mentioned.

As the substituent $R_4$, preferably, a hydrogen atom, a $C_1$ to $C_3$ alkyl group or phenyl may be mentioned.

The substituent $R_5$ and $R_6$ may independently represent a hydrogen atom. As the $C_1$ to $C_6$ linear or branched alkyl group which $R_5$ and $R_6$ independently represent, methyl, ethyl, propyl, isopropyl, butyl, sec-butyl, t-butyl, pentyl, hexyl, etc. may be mentioned. These groups may be substituted with a halogen atom; a hydroxy group; a cyano group; an amino group; a carboxyl group; a cycloalkyl group; a haloalkyl group; a carbamoyl group; an alkoxy group; an alkylcarbonyl group; or an aryl group which may include at least one hetero atom selected from an oxygen atom, a nitrogen atom and a sulfur atom. As the aryl group which $R_5$ and $R_6$ independently represent, phenyl, tolyl, naphthyl, 4-methylphenyl, 4-chlorophenyl, pyridyl, thiazolyl, thienyl, furyl, etc. may be mentioned. These groups may be substituted with a halogen atom; a hydroxy group; a cyano group; an amino group; a carboxyl group; an alkyl group; a cycloalkyl group; a haloalkyl group; a carbamoyl group; an alkoxy group; or an alkylcarbonyl group.

As the substituents $R_5$ and $R_6$, preferably, a hydrogen atom may be mentioned.

The compounds having the above formula (I) have asymmetric carbon atoms and include optical isomers. The optical isomers are also within the scope of the present invention. Further, the salts of the compounds having the above formula (I) and their optical isomers are also included in the present invention. As their salts, pharmacologically acceptable salts are preferable. As the pharmacologically acceptable salts, for example, inorganic acid salts such as hydrochlorides, hydrobromides, hydroiodides and phosphates, and organic acid salts such as oxalates, maleates, fumarates, lactates, malates, citrates, tartarates, benzoates, methanesulfonates, and p-toluenesulfonates, etc. may be mentioned.

Further, the present invention includes hydrates and solvates of the compounds having the above formula (I), and their optical isomers and their salts. As the solvent of the solvates, methanol, ethanol, isopropanol, butanol, acetone, ethyl acetate, chloroform, etc. may be mentioned.

The compounds having the above formula (I) may be produced by the following method combining known reactions. An example of the processes for production will be explained by the following reaction scheme.

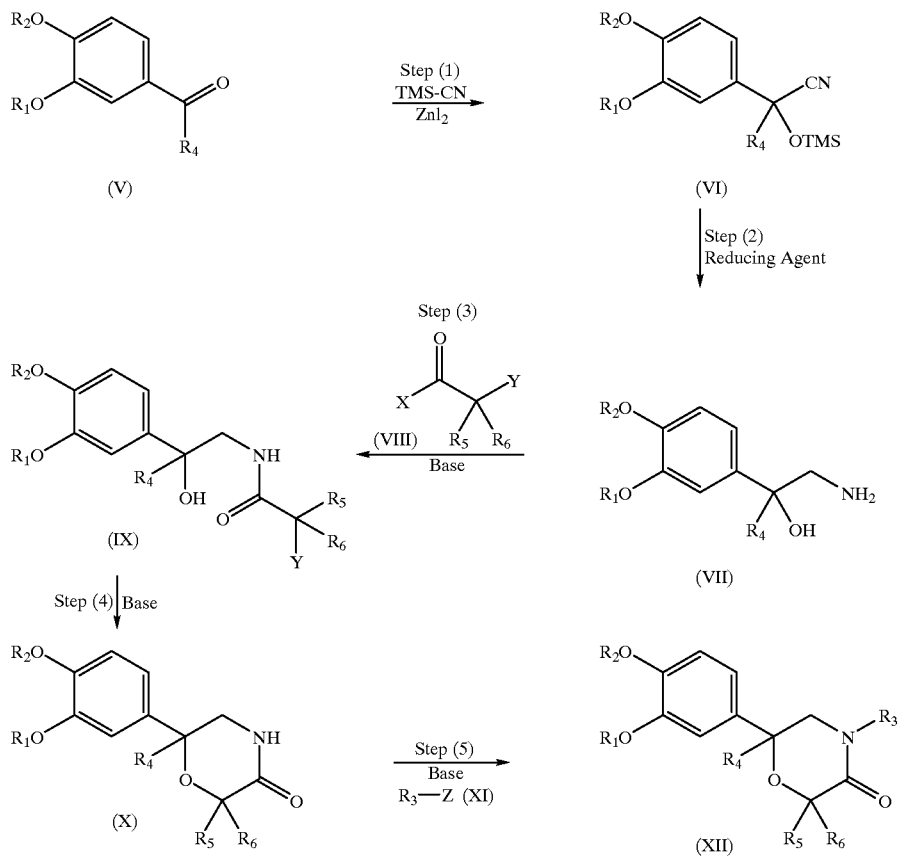

The compounds (X) and (XII) in the above reaction scheme correspond to compounds having the above formula (I).

Step (1): According to a known method [Philip Boudjouk et al., J. Chem. Soc. Chem. Comm., 54 (1973)], a ketone derivative (or an aldehyde derivative in the case where $R_4$ is a hydrogen atom) (V) was reacted with trimethylsilyl cyanate in the presence of a catalytic amount of zinc iodide to give a nitrile derivative (VI).

Step (2): According to a known method [W. E. Parham et al., Tetrahedron Letters, 923 (1971)], the nitrile derivative (VI) is converted to an amino alcohol derivative (VII) by a reducing agent such as lithium aluminum hydride.

Step (3): An amino alcohol derivative (VII) is reacted with an acetyl halide (VIII) (wherein X and Y indicate a halogen atom) in the presence of a base such as triethylamine or pyridine to give the compound (IX).

Step (4): The compound (IX) is intramolecularly condensed with a base such as sodium hydroxide, potassium hydroxide, sodium methoxide, potassium-t-butoxide or sodium hydride to obtain a ring-closed compound (X).

Step (5): The compound (X) is reacted with an alkyl halide (XI) (wherein Z indicates a halogen atom) in the presence of a base such as sodium hydride, whereby the compound (XII) is obtained.

The compounds obtained in the above steps are isolated by known methods (crystallization, recrystallization, chromatography, etc.), but the synthetic intermediates are sometimes used for the next steps without further purification.

The starting materials which may be used in the above reaction process may be commercially available products or may be synthesized from known compounds. For example, the ketone derivative (V) may be produced by a known method (see WO94/10118).

When the compound of the present invention is used as a therapeutic agent, it can be administered alone or together with a pharmacologically acceptable carrier. The composition is determined by the solubility of the compound, its chemical properties, the delivery route, medication plan, etc.

For example, it can be orally administered in the form of granules, powders, tablets, pills, hard gelatin capsules, soft gelatin capsules, syrups, emulsions, suspensions, liquids, etc. or can be administered by a non-oral route such as an injection (intravenous, intramuscular, or hypodermic), ointment, suppository, aerosol, etc. Alternatively, it may be made a powder for injection which is prepared at the time of use. Organic or inorganic solid or liquid carriers or diluents which are suitable for oral, rectal, non-oral, and topical administration can be used together with the compound of the invention. For example, in the case of oral administration, the compound can be prepared in the desired form by using an excipients such as lactose, D-glucose, corn starch, and sucrose, a disintegrants such as calcium carboxymethylcellulose, hydroxypropylcellulose, etc., a lubricants such as calcium stearate, magnesium stearate, talc, polyethylene glycol, and hydrogenated oil, a humectants such as hydroxypropylcellulose, hydroxypropylmethylcellulose, carboxymethylcellulose, polyvinyl alcohol, gelatin, and gum arabic, and a surfactant and flavoring agents if necessary.

When non-orally administered, it is possible to use a diluent such as water, ethanol, glycerine, propylene glycol, polyethylene glycol, agar, and tragacanth and, if necessary, use a solution adjuvant, buffering agent, preservative, flavoring agent, and colorant, etc. Pharmaceutical compositions may be prepared by general methods.

The clinical dosage generally ranges 0.01 to 1000 mg in terms of the compound of present invention per adult per day when orally administered, preferably 0.01 to 100 mg, but can be appropriately arranged depending upon the age, condition, symptoms, other drugs administered at the same time, etc. The daily dosage of the drug (compound of present invention) can be administered once a day or twice or three times a day with suitable intervals or intermittently. When administered by injection, one dosage in an amount of 0.001 to 100 mg per adult with or without intervals is preferable.

EXAMPLES

The present invention will be explained in detail below by Examples and Test Examples, but of course the present invention is not limited to these Examples and Test Examples.

Example 1

Synthesis of 2-(3,4-dimethoxyphenyl)morpholin-5-one (Compound No. 1 of Table 1)

(1) 2-amino-1-(3,4-dimethoxyphenyl)ethanol 3,4-dimethoxybenzaldehyde (2.00 g, 12.04 mM) and trimethylsilyl cyanate (1.57 g, 15.04 mM) were dissolved in dry methylene chloride (1 ml). While stirring at room temperature, zinc iodide (8.5 mg) was carefully added and the mixture was stirred for 2 hours. Next, the solution was dropwise added to a solution of lithium aluminum hydride (1.10 g, 28.88 mM) in dried tetrahydrofuran (120 ml) cooled to 0° C., then the reaction temperature was gradually warmed to room temperature and the mixture was stirred for 1 hour. Water (2 ml) was carefully added while cooling the reaction solution in an ice bath, the mixture was stirred for 1 hour, then the solution was filtered through Celite. The filtrate was dried over anhydrous magnesium sulfate, then the solvent was evaporated in vacuo to obtain a crude product (2.37 g) as a yellow solid. The crude product thus obtained had a sufficient purity even without purification, so could be used for the next reaction as it was.

$^1$H-NMR (400 MHz, CDCl$_3$) δ 2.81 (1H, dd, J=12.70, 7.81 Hz), 2.98 (1H, dd, J=12.70, 4.39 Hz), 3.87 (3H, s), 3.89 (3H, s), 4.58 (1H, dd, J=7.81, 4.39 Hz), 6.84 (1H, d, J=7.81 Hz), 6.87–6.92 (2H, m).

(2) 2-(2-chloroacetamido)-1-(3,4-dimethoxyphenyl) ethanol 2-amino-1-(3,4-dimethoxyphenyl)ethanol (2.38 g, 12.07 mM) and triethylamine (1.83 g, 18.10 mM) were dissolved in dry tetrahydrofuran (95 ml). While cooling to 0C, chloroacetylchloride (1.50 g, 13.27 mM) was added and the temperature was gradually warmed to room temperature. The mixture was stirred for one night, then the reaction solution was poured into ice water and was extracted with methylene chloride. The extract was dried over anhydrous sodium sulfate and the solvent was evaporated in vacuo to obtain a crude product of the above-described compound (3.30 g) as a brown oil. The crude product thus obtained could also be used as it was for the next reaction.

(3) 2-(3,4-dimethoxyphenyl)morpholin-5-one

A mixture of 2-(2-chloroacetamido)-1-(3,4-dimethoxyphenyl)ethanol (3.30 g, 12.06 mM) and potassium hydroxide (2.98 g, 45.21 mM) in ethanol (300 ml) heated to reflux for one night. Water was added into the reaction solution, the solution was extracted with methylene chloride, the extract was dried over anhydrous sodium sulfate, then the solvent was evaporated in vacuo to obtain a crude product as a brown solid. The crude product was purified by flash chromatography (SiO$_2$; eluted by gradient of range from ethyl acetate to 4% methanol/ethyl acetate), to obtain the above-described compound 1.47 g (yield 51.4%) as a light yellow solid.

$^1$H-NMR (400 MHz, CDCl$_3$) δ 3.48 (1H, ddd, J=12.21, 2.93, 2.93 Hz), 3.57 (1H, dd, J=12.21, 10.26 Hz), 3.89 (3H, s), 3.91 (3H, s), 4.35 (1H, d, J=16.60 Hz), 4.45 (1H, d, J=16.60 Hz), 4.72 (1H, dd, J=10.26, 2.93 Hz), 6.19 (1H, broad s), 6.86 (1H, d, J=8.30 Hz), 6.90 (1H, dd, J=8.30, 1.96 Hz), 6.94 (1H,d, J=1.96 Hz).

Example 2

Synthesis of 2-(3-cyclopentyloxy-4-methoxyphenyl) morpholin-5-one (Compound No. 2 of Table 1)
(1) 2-amino-1-(3-cyclopentyloxy-4-methoxyphenyl)ethanol
According to the same procedure as used in Example 1(1), using 3-cyclopentyloxy-4-methoxybenzaldehyde instead of 3,4-dimethoxybenzaldehyde, 2-amino-1-(3-cyclopentyloxy-4-methoxyphenyl)ethanol was obtained as a colorless oil.
$^1$H-NMR (400 MHz, CDCl$_3$) δ 1.57–1.64 (2H,m), 1.79–1.96 (6H,m), 2.80 (1H, dd, J=12.21, 7.81 Hz), 2.97 (1H, dd, J=12.21, 3.90 Hz), 3.84 (3H,s), 4.56 (1H, dd, J=7.81, 3.90 Hz), 4.79 (1H, m), 6.83 (1H, d, J=8.30 Hz), 6.86 (1H, dd, J=8.30, 1.47 Hz), 6.91 (1H, d, J=1.47 Hz).
(2) 2-(3-cyclopentyloxy-4-methoxyphenyl)morpholin-5-one
According to the same procedure as in Example 1(2) to (3), using 2-amino-1-(3-cyclopentyloxy-4-methoxyphenyl) ethanol instead of 2-amino-1-(3,4-dimethoxyphenyl) ethanol, the above-described compound (yield 42.7%) was obtained as a colorless solid.
$^1$H-NMR (400 MHz, CDCl$_3$) δ 1.56–1.65 (2H, m), 1.81–1.98 (6H, m), 3.46 (1H, ddd, J=12.20, 3.42, 3.42 Hz), 3.55 (1H, dd, J=12.20, 10.26 Hz), 3.84 (3H, s), 4.34 (1H, d, J=17.09 Hz), 4.44 (1H, d, J=17.09 Hz), 4.69 (1H, dd, J=10.26, 3.42 Hz), 4.80 (1H, m), 6.19 (1H, broad s), 6.85 (1H, d, J=8.30 Hz), 6.88 (1H, dd, J=8.30, 1.95 Hz), 6.93 (1H, d, J=1.95 Hz).

Example 3

Synthesis of 2-(3-benzyloxy-4-methoxyphenyl) morpholin-5-one (Compound No. 3 of Table 1)
(1) 2-amino-1-(3-benzyloxy-4-methoxyphenyl)ethanol
According to the same procedure as in Example 1(1), using 3-benzyloxy-4-methoxybenzaldehyde instead of 3,4-dimethoxybenzaldehyde, 2-amino-1-(3-benzyloxy-4-methoxyphenyl)ethanol was obtained as a yellow oil.
$^1$H-NMR (400 MHz, CDCl$_3$) δ 2.71 (1H, dd, J=12.70, 7.81 Hz), 2.85 (1H, dd, J=12.70, 3.90 Hz), 3.86 (3H, s), 4.49 (1H, dd, J=7.81, 3.90 Hz), 5.14 (2H, s), 6.83–6.92 (3H, m), 7.28–7.44 (5H, m).
(2) 2-(3-benzyloxy-4-methoxyphenyl)morpholin-5-one
According to the same procedure as used in Example 1(2), using 2-amino-1-(3-benzyloxy-4-methoxyphenyl)ethanol instead of 2-amino-1-(3,4-dimethoxyphenyl) ethanol, a crude product of 2-[(chloroacetyl)amido]-1-(3-benzyloxy-4-methoxyphenyl)ethanol was obtained. A mixture of the crude product and potassium t-butoxide in t-butanol was heated reflux for one night. Next, the reaction solution was cooled to room temperature, was poured into ice water, and was extracted with methylene chloride, the extract was dried over anhydrous sodium sulfate, then the solvent was evaporated in vacuo to obtain a crude product. The crude product obtained was purified by flash chromatography (SiO$_2$; eluted with 90% ethyl acetate/hexane) to obtain the above-described compound (yield 31.0%) as a light yellow solid.
$^1$H-NMR (400 MHz, CDCl$_3$) δ 3.41–3.51 (2H, m), 3.89 (3H, s), 4.32 (1H, d, J=16.60 Hz), 4.41 (1H, d, J=16.60 Hz), 4.66 (1H, dd, J=9.76, 3.41 Hz), 5.16 (2H, s), 6.35 (1H, s), 6.89 (1H, d, J=8.30 Hz), 6.92 (1H, dd, J=8.30, 1.96 Hz), 6.96 (1H, d, J=1.96 Hz), 7.28–7.39 (3H, m), 7.45 (2H, d, J=7.33 Hz).

Example 4

Synthesis of 2-(4-methoxy-3-phenethyloxyphenyl) morpholin-5-one (Compound No. 4 of Table 1)
(1) 4-methoxy-3-phenethyloxybenzaldehyde
Isovanillin (2.00 g, 13.14 mM), phenethyl alcohol (1.61 g, 13.14 mM), and triphenylphospine (4.14 g, 15.77 mM) were dissolved in dry tetrahydrofuran (50 ml). Diethyl azodicarboxylate (2.75 g, 15.77 mM) was carefully dropwise added to this solution at room temperature. The mixture was stirred at room temperature for one night, then this solution was diluted with diethyl ether (100 ml) and was successively washed with a aqueous sodium hydroxide and water. The organic solution was dried over anhydrous magnesium sulfate, and the solvent was evaporated in vacuo to obtain a residue as a light yellow oil. The residue was purified by flash chromatography (SiO$_2$: eluted by 25% ethyl acetate/hexane). The solvent was removed in vacuo and the product was dried to obtain 4-methoxy-3-phenethyloxybenzaldehyde 2.88 g (yield 85.5%) as a light yellow oil.
$^1$H-NMR (400 MHz, CDCl$_3$) δ 3.19 (2H, t, J=7.33 Hz), 4.28 (2H, t, J=7.33 Hz), 6.98 (1H, d, J=8.30 Hz), 7.23–7.35 (5H, m), 7.40 (1H, d, J=1.96 Hz), 7.46 (1H, dd, J=8.30, 1.96 Hz), 9.83 (1H, s)
(2) 2-amino-1-(4-methoxy-3-phenethyloxyphenyl)ethanol
According to the same procedure as used in Example 1(1), using 4-methoxy-3-phenethyloxybenzaldehyde instead of 3,4-dimethoxybenzaldehyde, 2-amino-1-(4-methoxy-3-phenethyloxyphenyl)ethanol was obtained as a yellow oil.
$^1$H-NMR (400 MHz, CDCl$_3$) δ 2.77 (1H, dd, J=12.70, 7.81 Hz), 2.95 (1H, dd, J=12.70, 3.90 Hz), 3.17 (2H, t, J=7.32 Hz), 3.86 (3H, s), 4.22 (2H, t, J=7.32 Hz), 4.54 (1H, dd, J=7.81, 3.90 Hz), 6.84–6.90 (3H, m), 7.22–7.34 (5H, m).
(3) 2-(4-methoxy-3-phenethyloxyphenyl)morpholin-5-one
According to the same procedure as used in Example 3(2), using 2-amino-1-(4-methoxy-3-phenethyloxyphenyl) ethanol instead of 2-amino-1-(3-benzyloxy-4-methoxyphenyl)ethanol, the above-described compound (yield 25.7%) was obtained as a light yellow solid.
$^1$H-NMR (400 MHz, CDCl$_3$) δ 3.17 (2H, t, J=7.32 Hz), 3.43 (1H, ddd, J=12.20, 3.42, 3.42 Hz), 3.51 (1H, dd, J=12.20, 10.25 Hz), 3.87 (3H, s), 4.22 (2H, t, J=7.32 Hz), 4.32 (1H, d, J=17.09 Hz), 4.41 (1H, d, J=17.09 Hz), 4.66 (1H, dd, J=10.25, 3.42 Hz), 6.49 (1H, broad s), 6.85–6.91 (3H, m), 7.23–7.34 (5H, m).

Example 5

Synthesis of 2-(3-butoxy-4-methoxyphenyl)morpholin-5-one (Compound No. 5 of Table 1)
(1) 3-butoxy-4-methoxybenzaldehyde
Isovanillin (6.00 g, 39.4 mM), butyl iodide (5.7 ml, 49.3 mM), and anhydrous potassium carbonate (6.8 g, 49.3 mM) were dissolved in dry dimethylformamide (50 ml), the mixture was stirred at room temperature for one night, then this solution was diluted with ethyl acetate (300 ml) and the mixture was washed with water. The organic solution was dried over anhydrous magnesium sulfate, and the solvent was evaporated in vacuo to obtain a residue as a light yellow oil. The residue was purified by flash chromatography (SiO$_2$: eluted by 20% ethyl acetate/hexane). The solvent was removed in vacuo and the result was dried to obtain 3-butoxy-4-methoxybenzaldehyde 8.09 g (yield 99.0%) as a light yellow oil.
$^1$H-NMR (400 MHz, CDCl$_3$) δ 0.99 (3H, t, J=7.32 Hz), 1.46–1.55 (2H, m), 1.82–1.89 (2H, m), 3.95 (3H, s), 4.08 (2H, t, J=6.83 Hz), 6.98 (1H, d, J=7.81 Hz), 7.40–7.46 (2H, m), 9.84 (1H, s).

(2) 2-amino-1-(3-butoxy-4-methoxyphenyl)ethanol

According to the same procedure as used in Example 1(1), using 3-butoxy-4-methoxybenzaldehyde instead of 3,4-dimethoxybenzaldehyde, 2-amino-1-(3-butoxy-4-methoxyphenyl)ethanol was obtained as a yellow oil.

$^1$H-NMR (400 MHz, CDCl$_3$) δ 0.98 (3H, t, J=7.32 Hz), 1.49 (2H, m), 1.82 (2H, m), 2.93–3.01 (2H, m), 3.85 (3H, s), 4.04 (2H, t, J=7.32 Hz), 4.71 (1H, m), 6.84–6.98 (3H, m).

(3) 2-(3-butoxy-4-methoxyphenyl)morpholin-5-one

According to the same procedure as used in Example 3(2), using 2-amino-1-(3-butoxy-4-methoxyphenyl)ethanol instead of 2-amino-1-(3-benzyloxy-4-methoxyphenyl)ethanol, the above-described compound (yield 51.2%) was obtained as a light yellow solid.

$^1$H-NMR (400 MHz, CDCl$_3$) δ 0.98 (3H, t, J=7.32 Hz), 1.50 (2H, m), 1.84 (2H, m), 3.47 (1H, ddd, J=12.21, 3.42, 3.42 Hz), 3.56 (1H, dd, J=12.21, 10.25 Hz), 3.86 (3H, s), 4.03 (1H, t, J=6.83 Hz), 4.34 (2H, d, J=17.09 Hz), 4.44 (1H, d, J=17.09 Hz), 4.70 (1H, dd, J=10.25, 3.42 Hz), 6.34 (1H, broad s), 6.86 (1H, d, J=8.30 Hz), 6.89 (1H, dd, J=8.30, 1.95 Hz), 6.94 (1H, d, J=1.95 Hz).

Example 6

Synthesis of 2-[3-(2-indanyloxy)-4-methoxyphenyl]morpholin-5-one (Compound No. 6 of Table 1)

(1) 3-(2-indanyloxy)-4-methoxybenzaldehyde

According to the same procedure as used in Example 4(1), using 2-indanol instead of phenethyl alcohol, 3-(2-indanyloxy)-4-methoxybenzaldehyde (yield 62.6%) was obtained as a light yellow solid.

$^1$H-NMR (400 MHz, CDCl$_3$) δ 3.25 (2H, dd, J=16.60, 3.42 Hz), 3.46 (2H, dd, J=16.60, 6.35 Hz), 3.90 (3H, s), 5.26 (1H, m), 6.98 (1H, d, J=8.30 Hz), 7.17–7.21 (2H, m), 7.22–7.25 (2H, m), 7.46–7.49 (2H, m), 9.87 (1H, s).

(2) 2-amino-1-[3-(2-indanyloxy)-4-methoxyphenyl]ethanol

According to the same procedure as used in Example 1(1), using 3-(2-indanyloxy)-4-methoxybenzaldehyde instead of 3,4-dimethoxybenzaldehyde, 2-amino-1-[3-(2-indanyloxy)-4-methoxyphenyl]ethanol was obtained as a yellow solid.

$^1$H-NMR (400 MHz, CDCl$_3$) δ 2.81 (1H, dd, J=12.70, 7.82 Hz), 3.00 (1H, dd, J=12.70, 3.91 Hz), 3.24 (2H, dd, J=16.60, 4.40 Hz), 3.38 (2H, dd, J=16.60, 6.83 Hz), 3.81 (3H, s), 4.58 (1H, dd, J=7.82, 3.91 Hz), 5.21 (1H, m), 6.86 (1H, d, J=8.30 Hz), 6.91 (1H, dd, J=8.30, 1.95 Hz), 6.98 (1H, d, J=1.95 Hz), 7.16–7.21 (2H, m), 7.22–7.24 (2H, m).

(3) 2-[3-(2-indanyloxy)-4-methoxyphenyl]morpholin-5-one

According to the same procedure as used in Example 3(2), using 2-amino-1-[3-(2-indanyloxy)-4-methoxyphenyl]ethanol instead of 2-amino-1-(3-benzyloxy-4-methoxyphenyl)ethanol, the above-described compound (yield 74.7%) was obtained as a light brown solid.

$^1$H-NMR (400 MHz, CDCl$_3$) δ 3.24 (2H, dd, J=16.60, 3.91 Hz), 3.39 (2H, dd, J=16.60, 6.35 Hz), 3.48 (1H, dm, J=12.20 Hz), 3.57 (1H, dd, J=12.20, 10.25 Hz), 3.82 (3H, s), 4.36 (1H, d, J=16.60 Hz), 4.45 (1H, d, J=16.60 Hz), 4.72 (1H, dd, J=10.25, 2.93 Hz), 5.21 (1H, m), 6.08 (1H, broad s), 6.87 (1H, d, J=8.30 Hz), 6.93 (1H, d, J=8.30, 1.47 Hz), 6.99 (1H, d, J=1.47 Hz), 7.17–7.25 (4H, m).

Example 7

Synthesis of 2-(3-cyclohexyloxy-4-methoxyphenyl)morpholin-5-one (Compound No. 7 of Table 1)

(1) 3-cyclohexyloxy-4-methoxybenzaldehyde

According to the same procedure as used in Example 4(1), using cyclohexanol instead of phenethyl alcohol, 3-cyclohexyloxy-4-methoxybenzaldehyde (yield 42.3%) was obtained as a light yellow oil.

$^1$H-NMR (400 MHz, CDCl$_3$) δ 1.23–1.43 (3H, m), 1.53–1.62 (3H, m), 1.81–1.85 (2H, m), 2.03–2.07 (2H, m), 3.93 (3H, s), 4.28–4.35 (1H, m), 6.97 (1H, d, J=8.79 Hz), 7.31–7.45 (2H, m), 9.84 (1H, s).

(2) 2-amino-1-[3-cyclohexyloxy-4-methoxyphenyl]ethanol

According to the same procedure as used in Example 1(1), using 3-cyclohexyloxy-4-methoxybenzaldehyde instead of 3,4-dimethoxybenzaldehyde, 2-amino-1-(3-cyclohexyloxy-4-methoxyphenyl)ethanol was obtained as a yellow oil.

$^1$H-NMR (400 MHz, CDCl$_3$) δ 1.25–1.41 (2H, m), 1.43–1.64 (4H, m), 1.80–1.82 (2H, m), 2.00–2.03 (2H, m), 2.79 (1H, dd, J=12.20, 7.81 Hz), 2.96 (1H, dd, J=12.20, 3.42 Hz), 3.84 (3H, s), 4.20 (1H, m), 4.55 (1H, dd, J=7.81, 3.42 Hz), 6.83–6.98 (3H, m).

(3) 2-(3-cyclohexyloxy-4-methoxyphenyl)morpholin-5-one

According to the same procedure as used in Example 3(2), using 2-amino-1-(3-cyclohexyloxy-4-methoxyphenyl)ethanol instead of 2-amino-1-(3-benzyloxy-4-methoxyphenyl)ethanol, the above-described compound (yield 31.9%) was obtained as a light brown solid.

$^1$H-NMR (400 MHz, CDCl$_3$) δ 1.26–1.40 (3H, m), 1.52–1.61 (3H, m), 1.81–1.84 (2H, m), 2.00–2.04 (2H, m), 3.46 (1H, ddd, J=11.72, 3.90, 3.90 Hz), 3.55 (1H, dd, J=12.21, 10.25 Hz), 3.85 (3H, s), 4.20 (1H, m), 4.34 (1H, d, J=17.09 Hz), 4.43 (1H, d, J=17.09 Hz), 4.68 (1H, dd, J=10.25, 3.90 Hz), 6.54 (1H, broad s), 6.87 (1H, d, J=8.30 Hz), 6.91 (1H, dd, J=8.30, 1.95 Hz), 6.95 (1H, d, J=1.95 Hz).

Example 8

Synthesis of 2-(3-cyclopropylmethoxy-4-methoxyphenyl)morpholin-5-one (Compound No. 8 of Table 1)

(1) 3-cyclopropylmethoxy-4-methoxybenzaldehyde

According to the same procedure as used in Example 4(1), using cyclopropylmethyl alcohol instead of phenethyl alcohol, 3-cyclopropylmethoxy-4-methoxybenzaldehyde (yield 77.4%) was obtained as a colorless solid.

$^1$H-NMR (400 MHz, CDCl$_3$) δ 0.36–0.40 (2H, m), 0.65–0.70 (2H, m), 1.34–1.38 (1H, m), 3.92 (2H, d, J=6.84 Hz), 3.97 (3H, s), 6.98 (1H, d, J=8.30 Hz), 7.39 (1H, d, J=1.95 Hz), 7.45 (1H, dd, J=8.30, 1.95 Hz), 9.84 (1H, s).

(2) 2-amino-1-(3-cyclopropylmethoxy-4-methoxyphenyl)ethanol

According to the same procedure as used in Example 1(1), using 3-cyclopropylmethoxy-4-methoxybenzaldehyde instead of 3,4-dimethoxybenzaldehyde, 2-amino-1-[3-cyclopropylmethoxy-4-methoxyphenyl]ethanol was obtained as a light brown solid. $^1$H-NMR (400 MHz, CDCl$_3$) δ 0.33–0.37 (2H, m), 0.61–0.66 (2H, m), 1.34 (1H, m), 2.79 (1H, dd, J=12.69, 7.81 Hz), 2.95 (1H, dd, J=12.69, 3.91 Hz), 3.86 (2H, d, J=6.84 Hz), 3.87 (3H, s), 4.55 (1H, dd, J=7.81, 3.91 Hz), 6.85–6.91 (3H, m).

(3) 2-(3-cyclopropylmethoxy-4-methoxyphenyl)morpholin-5-one

According to the same procedure as used in Example 3(2), using 2-amino-1-[3-cyclopropylmethoxy-4-methoxyphenyl]ethanol instead of 2-amino-1-(3-benzyloxy-4-methoxyphenyl)ethanol, the above-described compound (yield 52.0%) was obtained as a colorless solid.

$^1$H-NMR (400 MHz, CDCl$_3$) δ 0.36(2H, m), 0.65(2H, m), 1.34 (1H, m), 3.46 (1H, dt, J=12.20, 3.42 Hz), 3.54 (1H, dd, J=12.20, 9.77 Hz), 3.86 (2H, d, J=7.82 Hz), 3.88 (3H, s), 4.33 (1H, d, J=17.09 Hz), 4.42 (1H, d, J=17.09 Hz), 4.68 (1H, dd, J=9.77, 3.42 Hz), 6.86 (1H, d, J=8.30 Hz), 6.89 (1H, dd, J=8.30, 1.46 Hz), 6.92 (1H, d, J=1.46 Hz), 6.99 (1H, broad s).

Example 9

Synthesis of 2-(3,4-dimethoxyphenyl)-2-methylmorpholin-5-one (Compound No. 9 of Table 1)

(1) 2-amino-1-(3,4-dimethoxyphenyl)-1-methylethanol

According to the same procedure as used in Example 1(1), using 3,4-dimethoxyacetophenone instead of 3,4-dimethoxybenzaldehyde, 2-amino-1-(3,4-dimethoxyphenyl)-1-methylethanol was obtained as a yellow oil.

$^1$H-NMR (400 MHz, CDCl$_3$) δ 1.47 (3H, s), 2.78 (1H, d, J=12.20 Hz), 3.06 (1H, d, J=12.20 Hz), 3.87 (3H, s), 3.90 (3H, s), 6.85 (1H, d, J=8.30 Hz), 6.91 (1H, dd, J=8.30, 1.95 Hz), 7.05 (1H, d, J=1.95 Hz).

(2) 2-(3,4-dimethoxyphenyl)-2-methylmorpholin-5-one

According to the same procedure as used in Example 3(2), using 2-amino-1-(3,4-dimethoxyphenyl)-1-methylethanol instead of 2-amino-1-(3-benzyloxy-4-methoxyphenyl) ethanol, the above-described compound (yield 32.4%) was obtained as a light yellow solid.

1H-NMR (400 MHz, CDCl$_3$) δ 1.56 (3H, s), 3.61 (1H, dd, J=12.70, 1.96 Hz), 3.84 (1H, dd, J=12.70, 3.90 Hz), 3.88 (3H, S), 3.90 (3H, s), 4.01 (1H, d, J=17.09 Hz), 4.20 (1H, d, J=17.09 Hz), 6.14 (1H, broad), 6.84 (1H, d, J=8.30 Hz), 6.90 (1H, dd, J=8.30, 1.95 Hz), 6.99 (1H, d, J=1.95 Hz).

Example 10

Synthesis of 2-(3-cyclopentyloxy-4-methoxyphenyl)-2-methylmorpholin-5-one (Compound No. 10 of Table 1)

(1) 3-cyclopentyloxy-4-methoxyacetophenone

A solution of 3-cyclopentyloxy-4-methoxybenzaldehyde (10.00 g, 45.40 mM) in dry tetrahydrofuran (100 ml) was cooled to 0° C., then a tetrahydrofuran solution of methyl magnesium bromide (136.20 mM) was dropwise added to the solution and the mixture was stirred at that temperature for 2 hours. An aqueous ammonium chloride was added to the solution obtained, which was then warmed to room temperature and extracted with ethyl acetate, then the extract was successively washed with brine and water. The organic solution was dried over anhydrous magnesium sulfate, and the solvent was evaporated in vacuo to obtain a crude product of 1-(3-cyclopentyloxy-4-methoxyphenyl)ethanol (10.67 g) as a light yellow oil. The crude product thus obtained of 1-(3-cyclopentyloxy-4-methoxyphenyl)ethanol (10.67 g) was dissolved in dry methylene chloride (200 ml), manganese dioxide (39.2 g) was added to the solution, then the solution was vigorously stirred at room temperature for 16 hours. The undissolved material in the solution was removed by filtration through Celite, and the filtrate was concentrated in vacuo to obtain a residue as a yellow oil. The residue was purified by flash chromatography (SiO$_2$: eluted with 25% ethyl acetate/hexane). The solvent was removed in vacuo and the resultant product was dried to obtain 3-cyclopentyloxy-4-methoxyacetophenone 10.00 g (yield 94.4%) as a yellow oil.

$^1$H-NMR (400 MHz, CDCl$_3$) δ 1.61–1.64 (2H, m), 1.81–1.90 (4H, m), 1.97–2.00 (2H, m), 2.56 (3H, s), 3.91 (3H, s), 4.86 (1H, m), 6.87 (1H, d, J=8.30 Hz), 7.52 (1H, d, J=1.95 Hz), 7.55 (1H, dd, J=8.30, 1.95 Hz).

(2) 2-amino-1-(3-cyclopentyloxy-4-methoxyphenyl)-1-methylethanol

According to the same procedure as used in Example 1(1), using 3-cyclopentyloxy-4-methoxyacetophenone instead of 3,4-dimethoxybenzaldehyde, 2-amino-1-(3-cyclopentyloxy-4-methoxyphenyl)-1-methylethanol was obtained as a brown oil.

$^1$H-NMR (400 MHz, CDCl$_3$) δ 1.47 (3H, s), 1.56–1.66 (2H, m), 1.79–1.97 (6H, m), 2.75 (1H, d, J=12.20 Hz), 3.05 (1H, d, J=12.20 Hz), 3.84 (3H, s), 4.79–4.83 (1H, m), 6.83 (1H, d, J=8.30 Hz), 6.90 (1H, dd, J=8.30, 2.44 Hz), 7.02 (1H, d, J=2.44 Hz).

(3) 2-(3-cyclopentyloxy-4-methoxyphenyl)-2-methylmorpholin-5-one According to the same procedure as used in Example 3(2), using 2-amino-1-(3-cyclopentyloxy-4-methoxyphenyl)-1-methylethanol instead of 2-amino-1-(3-benzyloxy-4-methoxyphenyl)ethanol, the above-described compound (yield 36.7%) was obtained as a light brown solid.

$^1$H-NMR (400 MHz, CDCl$_3$) δ 1.53 (3H, s), 1.60–1.64 (2H, m), 1.81–1.94 (6H, m), 3.60 (1H, dd, J=12.70, 1.47 Hz), 3.81–3.86 (1H, m), 3.84 (3H, s), 3.98 (1H, d, J=17.58 Hz), 4.18 (1H, d, J=17.58 Hz), 4.79 (1H, m), 6.46 (1H, broad s), 6.83 (1H, d, J=8.30 Hz), 6.88 (1H, dd, J=8.30, 1.95 Hz), 6.98 (1H, d, J=1.95 Hz).

Example 11

2-(3-cyclopentyloxy-4-methoxyphenyl)-2-phenylmorpholin-5-one (Compound No. 11 of Table 1)

(1) 3-cyclopentyloxy-4-methoxybenzophenone

A solution of 3-cyclopentyloxy-4-methoxybenzaldehyde (10.00 g, 45.40 mM) in dry tetrahydrofuran (50 ml) was cooled to −78° C., a toluene solution of phenyllithium (49.94 mM) was dropped into this solution, and the resultant mixture was stirred at that temperature for 5 hours. Water was added to the solution obtained, the solution was warmed to room temperature and extracted with diethyl ether, the extract was dried over anhydrous magnesium sulfate, then the solvent was removed in vacuo to obtain a crude product of α-(3-cyclopentyloxy-4-methoxyphenyl)benzyl alcohol 13.56 g as a yellow oil. The crude product thus obtained of α-(3-cyclopentyloxy-4-methoxyphenyl)benzyl alcohol in an amount of 10.00 g was dissolved in dry methylene chloride (110 ml), manganese dioxide (16.00 g) was added to the solution, and the solution was vigorously stirred at room temperature for 2 days. The undissolved material in the solution obtained were removed by filtration through Celite, and the filtrate was concentrated in vacuo to obtain a residue as a yellow solid. The residue was purified by flash chromatography (SiO$_2$: eluted with 20% ethyl acetate/hexane). The solvent was removed in vacuo and the product was dried to obtain 3-cyclopentyloxy-4-methoxybenzophenone 9.20 g (yield 92.6%) as a light yellow solid.

$^1$H-NMR (400 MHz, CDCl$_3$) δ 1.60–1.65 (2H, m), 1.82–2.00 (6H, m), 3.93 (3H, s), 4.84 (1H, m), 6.89 (1H, d, J=8.30 Hz), 7.38 (1H, dd, J=8.30, 1.95 Hz), 7.46 (1H, d, J=1.95 Hz), 7.49 (2H, d, J=7.81 Hz), 7.55–7.59 (1H, m), 7.75–7.77 (2H, m).

(2) 2-amino-1-(3-cyclopentyloxy-4-methoxyphenyl)-1-phenylethanol

According to the same procedure as used in Example 1(1), using 3-cyclopentyloxy-4-methoxybenzophenone instead of 3,4-dimethoxybenzaldehyde, 2-amino-1-(3-cyclopentyloxy-4-methoxyphenyl)-1-phenylethanol was obtained as a yellow solid.

$^1$H-NMR (400 MHz, CDCl$_3$) δ 1.54–1.61 (2H, m), 1.78–1.86 (6H, m), 3.33–3.38 (2H, m), 3.82 (3H, s), 4.73 (1H, m), 6.80 (1H, d, J=8.30 Hz), 6.90 (1H, dd, J=8.30, 1.95 Hz), 7.01 (1H, d, J=1.95 Hz), 7.21–7.24 (1H, m), 7.32 (2H, t, J=7.33 Hz), 7.42–7.44 (2H, m).

(3) 2-(3-cyclopentyloxy-4-methoxyphenyl)-2-phenylmorpholin-5-one

According to the same procedure as used in Example 3(2), using 2-amino-1-(3-cyclopentyloxy-4-methoxyphenyl)-1-phenylethanol instead of 2-amino-1-(3-benzyloxy-4-methoxyphenyl)ethanol, the above-described compound (yield 32.8%) was obtained as a light yellow solid.

$^1$H-NMR (400 MHz, CDCl$_3$) δ 1.56–1.60 (2H, m), 1.74–1.88 (6H, m), 3.83 (3H, s), 3.89 (1H, dd, J=12.69, 1.95

Hz), 3.94 (1H, dd, J=12.69, 1.95 Hz), 4.10 (1H, d, J=17.09 Hz), 4.16 (1H, d, J=17.09 Hz), 4.68 (1H, m), 6.57 (1H, broad s), 6.80 (1H, d, J=8.79 Hz), 6.83–6.86 (2H, m), 7.26–7.34 (5H, m).

Example 12

Synthesis of 2-(3.4-dimethoxyphenyl)-4-methylmorpholin-5-one (Compound No. 12 of Table 1)

2-(3,4-dimethoxyphenyl)morpholin-5-one (0.10 g, 0.42 mM) produced in Example 1, sodium hydride (60%) (0.02 g, 0.46 mM), and methyl iodide (0.07 g, 0.51 mM) were dissolved in dry N,N-dimethylformamide (2 ml) and the mixture was stirred at room temperature for one night. Water was added to the reaction solution, the solution was extracted with methylene chloride, the extract was dried over anhydrous sodium sulfate, then the solvent was removed in vacuo to obtain a crude product as a yellow oil. The crude product was purified by flash chromatography ($SiO_2$: eluted by 3% methanol/methylene chloride) to obtain the above-described compound (yield 96.9%) as a colorless solid.

$^1$H-NMR (400 MHz, $CDCl_3$) δ 3.02 (3H, s), 3.33 (1H, dd, J=12.20, 2.93 Hz), 3.57 (1H, dd, J=12.20, 10.75 Hz), 3.89 (3H, s), 3.91 (3H, s), 4.32 (1H, d, J=16.60 Hz), 4.42 (1H, d, J=16.60 Hz), 4.77 (1H, d, J=10.75, 2.93 Hz), 6.86 (1H, d, J=8.30 Hz), 6.90 (1H, dd, J=8.30, 1.46 Hz), 6.94 (1H, d, J=1.46 Hz).

Example 13

Synthesis of 4-(4-bromobenzyl)-2-(3-cyclopentyloxy-4-methoxyphenyl)morpholin-5-one (Compound No. 13 of Table 1)

According to the same procedure as used in Example 12, using the 2-(3-cyclopentyloxy-4-methoxyphenyl) morpholin-5-one produced in Example 2 instead of 2-(3,4-dimethoxyphenyl)morpholin-5-one, and using 4-bromobenzyl bromide instead of methyl iodide, the above-described compound (yield 96.5%) was obtained as a brown oil.

$^1$H-NMR (400 MHz, $CDCl_3$) δ 1.56–1.66 (2H, m), 1.77–1.95 (6H, m), 3.22 (1H, dd, J=12.21, 2.93 Hz), 3.41 (1H, dd, J=12.21, 10.26 Hz), 3.82 (3H, s), 4.37 (1H, d, J=16.60 Hz), 4.48 (1H, d, J=16.60 Hz), 4.48 (1H, d, J=15.14 Hz), 4.67 (1H, d, J=15.14 Hz), 4.68 (1H, dd, J=10.26, 2.93 Hz), 4.76 (1H, m), 6.78–6.87 (3H, m), 7.17 (2H, d, J=8.30 Hz), 7.47 (2H, d, J=8.30 Hz).

Example 14

Synthesis of 2-(3-cyclopentyloxy-4-methoxyphenyl)-4-methylmorpholin-5-one (Compound No. 14 of Table 1)

According to the same procedure as used in Example 13, using methyl iodide instead of 4-bromobenzyl bromide, the above-described compound (yield 92.5%) was obtained as a light brown solid.

$^1$H-NMR (400 MHz, $CDCl_3$) δ 1.58–1.67 (2H, m), 1.72–2.00 (6H, m), 3.02 (3H, s), 3.32 (1H, dd, J=12.21, 3.42 Hz), 3.55 (1H, dd, J=12.21, 10.74 Hz), 3.84 (3H, s), 4.30 (1H, d, J=16.60 Hz), 4.40 (1H, d, J=16.60 Hz), 4.74 (1H, dd, J=10.74, 3.42 Hz), 4.80 (1H, m), 6.84–6.93 (3H, m).

Example 15

Synthesis of 2-(3-cyclopentyloxy-4-methoxyphenyl)-4-ethoxycarbonylmethylmorpholin-5-one (Compound No. 15 of Table 1)

According to the same procedure as used in Example 13, using ethyl bromoacetate instead of 4-bromobenzyl bromide, the above-described compound (yield 74.5%) was obtained as a light brown solid.

$^1$H-NMR (400 MHz, $CDCl_3$) δ 1.30 (3H, t, J=7.33 Hz), 1.60–1.67 (2H, m), 1.81–1.96 (6H, m), 3.38 (1H, dd, J=11.74, 2.93 Hz), 3.67 (1H, dd, J=11.74, 10.74 Hz), 3.84 (3H, s), 4.08 (1H, d, J=17.09 Hz), 4.22 (2H, q, J=7.33 Hz), 4.27 (1H, d, J=17.09 Hz), 4.38 (1H, d, J=17.09 Hz), 4.47 (1H, d, J=17.09 Hz), 4.80 (1H, m), 4.83 (1H, dd, J=10.74, 2.93 Hz), 6.84 (1H, d, J=8.30 Hz), 6.90 (1H, dd, J=8.30, 1.95 Hz), 6.94 (1H, d, J=1.95 Hz).

Example 16

Synthesis of 2-(3-cyclopentyloxy-4-methoxyphenyl)-4-(4-pyridylmethyl)morpholin-5-one (Compound No. 16 of Table 1)

According to the same procedure as used in Example 13, using 4-chloromethylpyridine hydrochloride instead of 4-bromobenzyl bromide, the above-described compound (yield 73.3%) was obtained as a brown oil.

$^1$H-NMR (400 MHz, $CDCl_3$) δ 1.58–1.64 (2H, m), 1.73–1.96 (6H, m), 3.24 (1H, dd, J=12.21, 3.42 Hz), 3.48 (1H, dd, J=12.21, 11.23 Hz), 3.83 (3H, s), 4.41 (1H, d, J=16.60 Hz), 4.53 (1H, d, J=16.60 Hz), 4.54 (1H, d, J=14.65 Hz), 4.73 (1H, d, J=14.65 Hz), 4.73 (1H, dd, J=11.23, 3.42 Hz), 4.77 (1H, m), 6.82–6.93 (3H, m), 7.22 (2H, d, J=5.37 Hz), 8.60 (2H, d, J=5.37 Hz).

Example 17

Synthesis of 2-(3-cyclopentyloxy-4-methoxyphenyl)-4-ethylmorpholin-5-one (Compound No. 17 of Table 1)

According to the same procedure as used in Example 13, using ethyl iodide instead of 4-bromobenzyl bromide, the above-described compound (yield 44.2%) was obtained as a light brown oil.

$^1$H-NMR (400 MHz, $CDCl_3$) δ 1.19 (3H, t, J=7.32 Hz), 1.60–1.64 (2H, m), 1.82–1.96 (6H, m), 3.30 (1H, dd, J=12.21, 2.93 Hz), 3.42 (1H, dq, J=14.65, 7.32 Hz), 3.53 (1H, dd, J=12.21, 10.26 Hz), 3.56 (1H, dq, J=14.65, 7.32 Hz), 3.85 (3H, s), 4.30 (1H, d, J=16.60 Hz), 4.40 (1H, d, J=16.60 Hz), 4.72 (1H, dd, J=10.26, 2.93 Hz), 4.81 (1H, m), 6.85 (1H, d, J=8.30 Hz), 6.89 (1H, dd, J=8.30, 1.96 Hz), 6.93 (1H, d, J=1.96 Hz).

Example 18

Synthesis of 2-(3-cyclopentyloxy-4-methoxyphenyl)-4-(2-quinolylmethyl)morpholin-5-one (Compound No. 18 of Table 1)

According to the same procedure as used in Example 13, using 2-chloromethylquinoline hydrochloride instead of 4-bromobenzyl bromide, the above-described compound (yield 27.4%) was obtained as a yellow oil.

$^1$H-NMR (400 MHz, $CDCl_3$) δ 1.52–1.63 (2H, m), 1.73–1.96 (6H, m), 3.51 (1H, dd, J=12.70, 3.42 Hz), 3.61 (1H, dd, J=12.70, 10.25 Hz), 3.80 (3H, s), 4.43 (1H, d, J=16.60 Hz), 4.54 (1H, d, J=16.60 Hz), 4.74 (1H, m), 4.77 (1H, dd, J=10.25, 3.42 Hz), 4.87 (1H, d, J=15.14 Hz), 5.04 (1H, d, J=15.14 Hz), 6.78 (1H, d, J=8.30 Hz), 6.81 (1H, dd, J=8.30, 1.95 Hz), 6.88 (1H, d, J=1.95 Hz), 7.50 (1H, d, J=8.30 Hz), 7.55 (1H, d, J=7.32 Hz), 7.72 (1H, m), 7.82 (1H, d, J=8.30 Hz), 8.03 (1H, d, J=8.31 Hz), 8.17 (1H, d, J=8.30 Hz).

Example 19

Synthesis of 4-butyl-2-(3-cyclopentyloxy-4-methoxyphenyl)morpholin-5-one (Compound No. 19 of Table According to the same procedure as used in Example 13, using butyl iodide instead of 4-bromobenzyl bromide, the above-described compound (yield 58.1%) was obtained as a yellow oil.

$^1$H-NMR (400 MHz, CDCl$_3$) δ 0.95 (3H, t, J=7.32 Hz), 1.36 (2H, q, J=7.32 Hz), 1.53–1.64 (4H, m), 1.80–1.97 (6H, m), 3.30 (1H, dd, J=12.21, 3.42 Hz), 3.34–3.38 (1H, m), 3.51 (1H, dd, J=12.21, 10.26 Hz), 3.47–3.53 (1H, m), 3.85 (3H, s), 4.30 (1H, d, J=16.61 Hz), 4.41 (1H, d, J=16.61 Hz), 4.71 (1H, dd, J=10.26, 3.42 Hz), 4.81 (1H, m), 6.85 (1H, d, J=8.30 Hz), 6.88 (1H, dd, J=8.30, 1.95 Hz), 6.93 (1H, d, J=1.95 Hz).

Example 20

Synthesis of 4-acetyl-2-(3-cyclopentyloxy-4-methoxyphenyl)morpholin-5-one (Compound No. 20 of Table According to the same procedure as used in Example 13, using acetyl bromide instead of 4-bromobenzyl bromide, the above-described compound (yield 33.5%) was obtained as a colorless solid.

$^1$H-NMR (400 MHz, CDCl$_3$) δ 1.57–1.63 (2H, m), 1.81–1.95 (6H, m), 2.62 (3H, s), 3.53 (1H, dd, J=13.68, 10.74 Hz), 3.85 (3H, s), 4.18 (1H, dd, J=13.68, 2.93 Hz), 4.38 (1H, d, J=17.58 Hz), 4.53 (1H, d, J=17.58 Hz), 4.70 (1H, dd, J=10.74, 2.93 Hz), 4.78 (1H, m), 6.85 (1H, d, J=8.30 Hz), 6.88 (1H, dd, J=8.30, 1.95 Hz), 6.91 (1H, d, J=1.95 Hz).

Example 21

Synthesis of 2-[3-(2-indanyloxy)-4-methoxyphenyl]-4-methylmorpholin-5-one (Compound No. 21 of Table 1)

According to the same procedure as used in Example 12, using the 2-[3-(2-indanyloxy)-4-methoxyphenyl]morpholin-5-one produced in Example 6 instead of 2-(3,4-dimethoxyphenyl)morpholin-5-one, the above-described compound (yield 100%) was obtained as a light yellow solid.

$^1$H-NMR (400 MHz, CDCl$_3$) δ 3.03 (3H, s), 3.24 (2H, dd, J=16.60, 3.90 Hz), 3.34 (1H, dd, J=12.69, 3.42 Hz), 3.39 (2H, dd, J=16.60, 6.84 Hz), 3.57 (1H, dd, J=12.69, 10.74 Hz), 3.82 (3H, s), 4.32 (1H, d, J=16.60 Hz), 4.42 (1H, d, J=16.60 Hz), 4.77 (1H, dd, J=10.74, 3.42 Hz), 5.22 (1H, m), 6.87 (1H, d, J=8.30 Hz), 6.93 (1H, dd, J=8.30, 1.95 Hz), 7.00 (1H, d, J=1.95 Hz), 7.16–7.20 (2H, m), 7.22–7.25 (2H, m).

Example 22

Synthesis of 2-(3-cyclopentyloxy-4-methoxyphenyl)-4-methyl-2-phenylmorpholin-5-one (Compound No. 22 of Table 1)

According to the same procedure as used in Example 12, using the 2-(3-cyclopentyloxy-4-methoxyphenyl)-2-phenylmorpholin-5-one produced in Example 11 instead of 2-(3,4-dimethoxyphenyl)morpholin-5-one, the above-described compound (yield 64.7%) was obtained as a yellow oil.

$^1$H-NMR (400 MHz, CDCl$_3$) δ 1.52–1.60 (2H, m), 1.80–1.81 (6H, m), 3.08 (3H, s), 3.83 (3H, s), 3.85 (2H, s), 4.06 (1H, d, J=17.09 Hz), 4.12 (1H, d, J=17.09 Hz), 4.68 (11H, m), 6.75 (1H, dd, J=8.79, 1.95 Hz), 6.80 (1H, d, J=8.79 Hz), 6.83 (1H, d, J=1.95 Hz), 7.27–7.35 (5H, m).

Example 23

Synthesis of 2-(3-cyclopentyloxy-4-methoxyphenyl)-2-phenyl-4-(4-pyridylmethyl)morpholin-5-one (Compound No. 23 of Table 1)

According to the same procedure as used in Example 22, using 4-chloromethylpyridine hydrochloride instead of methyl iodide, the above-described compound (yield 89.8%) was obtained as a light yellow solid.

$^1$H-NMR (400 MHz, CDCl$_3$) δ 1.55–1.65 (2H, m), 1.78 (6H, m), 3.76 (1H, d, J=12.69 Hz), 3.79 (1H, d, J=12.69 Hz), 3.81 (3H, s), 4.21 (1H, d, J=17.09 Hz), 4.25 (1H, d, J=17.09 Hz), 4.61 (1H, m), 4.62 (1H, d, J=15.13 Hz), 4.68 (1H, d, J=15.13 Hz), 6.53 (1H, dd, J=8.30, 1.95 Hz), 6.69 (1H, d, J=8.30 Hz), 6.76 (1H, d, J=1.95 Hz), 7.15–7.17 (2H, m), 7.24–7.30 (5H, m), 8.62–8.63 (2H, m).

Example 24

Synthesis of 2-[3-(2-indanyloxy)-4-methoxyphenyl]-2-phenylmorpholin-5-one (Compound No. 24 of Table 1)

(1) 3-(2-indanyloxy)-4-methoxybenzophenone

According to the same procedure as used in Example 11(1), using the 3-(2-indanyloxy)-4-methoxybenzaldehyde produced in Example 6(1) instead of 3-cyclopentyloxy-4-methoxybenzaldehyde, 3-(2-indanyloxy)-4-methoxybenzophenone (yield 87.3%) was obtained as a light yellow solid.

$^1$H-NMR (400 MHz, CDCl$_3$) δ 3.26 (2H, dd, J=16.60, 3.42 Hz), 3.43 (2H, dd, J=16.60, 6.34 Hz), 3.89 (3H, s), 5.26 (1H, m), 6.90 (1H, d, J=8.30 Hz), 7.17–7.20 (2H, m), 7.22–7.26 (2H, m), 7.42 (1H, dd, J=8.30, 1.95 Hz), 7.47–7.51 (2H, m), 7.54 (1H, d, J=1.95 Hz), 7.56–7.60 (1H, m), 7.77–7.79 (2H, m).

(2) 2-amino-1-[3-(2-indanyloxy)-4-methoxyphenyl]-1-phenylethanol

According to the same procedure as used in Example 1(1), using 3-(2-indanyloxy)-4-methoxybenzophenone instead of 3,4-dimethoxybenzaldehyde, 2-amino-1-(3-(2-indanyloxy)-4-methoxyphenyl)-1-phenylethanol was obtained as a yellow solid.

$^1$H-NMR (400 MHz, CDCl$_3$) δ 3.17 (1H, dd, J=16.60, 3.91 Hz), 3.18 (1H, dd, J=16.60, 3.91 Hz), 3.30 (1H, dd, J=16.60, 6.84 Hz), 3.31 (1H, dd, J=16.60, 6.84 Hz), 3.36 (2H, broad), 3.79 (3H, s), 5.15 (1H, m), 6.82 (1H, d, J=8.30 Hz), 6.96 (1H, dd, J=8.30, 1.95 Hz), 7.07 (1H, d, J=1.95 Hz), 7.15–7.25 (5H, m), 7.32–7.36 (2H, m), 7.45 (2H, d, J=7.33 Hz).

(3) 2-[3-(2-indanyloxy)-4-methoxyphenyl]-2-phenylmorpholin-5-one

According to the same procedure as used in Example 3(2), using 2-amino-1-[3-(2-indanyloxy)-4-methoxyphenyl]-1-phenylethanol instead of 2-amino-1-(3-benzyloxy-4-methoxyphenyl)ethanol, the above-described compound (yield 68.0%) was obtained as a light brown solid.

$^1$H-NMR (400 MHz, CDCl$_3$) δ 3.14 (2H, dm, J=16.60 Hz), 3.25 (1H, dd, J=16.60, 6.35 Hz), 3.28 (1H, dd, J=16.60, 6.35 Hz), 3.80 (3H, s), 3.91 (1H, dd, J=13.18, 2.93 Hz), 3.95 (1H, dd, J=13.18, 2.93 Hz), 4.13 (1H, d, J=17.09 Hz), 4.17 (1H, d, J=17.09 Hz), 5.11 (1H, m), 6.51 (1H, broad s), 6.82 (1H, d, J=8.30 Hz), 6.89–6.91 (2H, m), 7.15–7.22 (4H, m), 7.27–7.33 (1H, m), 7.36 (4H, m).

Example 25

Synthesis of 2-[3-(2-indanyloxy)-4-methoxyphenyl]-4-methyl-2-phenylmorpholin-5-one (Compound No. 25 of Table 1)

According to the same procedure as used in Example 12, using the 2-[3-(2-indanyloxy)-4-methoxyphenyl]-2-phenylmorpholin-5-one produced in Example 24 instead of 2-(3,4-dimethoxyphenyl)morpholin-5-one, the above-described compound (yield 75.5%) was obtained as a colorless solid.

¹H-NMR (400 MHz, CDCl₃) δ 3.09 (3H, s), 3.14 (2H, dd, J=16.60, 3.91 Hz), 3.25 (1H, dd, J=16.60, 6.83 Hz), 3.27 (1H, dd, J=16.60, 6.83 Hz), 3.80 (3H, s), 3.86 (2H, s), 4.09 (1H, d, J=16.60 Hz), 4.15 (1H, d, J=16.60 Hz), 5.08–5.12 (1H, m), 6.82 (1H, s), 6.82 (1H, s), 6.88 (1H, s), 7.15–7.34 (9H, m).

Example 26

Synthesis of 2-[4-methoxy-3-(5-phenylpentyloxy) phenyl]morpholin-5-one (Compound No. 26 of Table 1)

(1) 4-methoxy-3-(5-phenylpentyloxy)benzaldehyde

According to the same procedure as used in Example 4(1), using 5-phenylpentanol instead of phenethyl alcohol, 4-methoxy-3-(5-phenylpentyloxy)benzaldehyde (yield 81.4%) was obtained as a light yellow solid.

¹H-NMR (400 MHz, CDCl₃) δ 1.47–1.59 (2H, m), 1.67–1.75 (2H, m), 1.87–1.94 (2H, m), 2.65 (2H, t, J=7.81 Hz), 3.94 (3H, s), 4.07 (2H, t, J=6.83 Hz), 6.96–7.56 (8H, m), 9.84 (1H, s).

(2) 2-amino-1-(5-phenylpentyloxy-4-methoxyphenyl) ethanol

According to the same procedure as used in Example 1(1), using 4-methoxy-3-(5-phenylpentyloxy)benzaldehyde instead of 3,4-dimethoxybenzaldehyde, 2-amino-1-(5-phenylpentyloxy-4-methoxyphenyl)ethanol was obtained as a light yellow solid.

¹H-NMR (400 MHz, CDCl₃) δ 1.48–1.55 (2H, m), 1.66–1.74 (2H, m), 1.84–1.92 (2H, m), 2.64 (2H, t, J=6.84 Hz), 2.79 (1H, dd, J=12.70, 7.32 Hz), 2.98 (1H, dd, J=12.70, 3.90 Hz), 3.85 (3H, s), 4.02 (2H, t, J=6.84 Hz), 4.56 (1H, dd, J=7.32, 3.90 Hz), 6.81–6.98 (3H, m), 7.16–7.30 (5H, m).

(3) 2-(5-phenylpentyloxy-4-methoxyphenyl)morpholin-5-one

According to the same procedure as used in Example 3(2), using 2-amino-1-(5-phenylpentyloxy-4-methoxyphenyl) ethanol instead of 2-amino-1-(3-benzyloxy-4-methoxyphenyl)ethanol, the above-described compound (yield 45.6%) was obtained as a light yellow solid.

¹H-NMR (400 MHz, CDCl₃) δ 1.50–1.55 (2H, m), 1.66–1.73 (2H, m), 1.87–1.91 (2H, m), 2.65 (2H, t, J=7.81 Hz), 3.45–3.48 (1H, m), 3.53–3.58 (1H, m), 3.86 (3H, s), 4.02 (2H, t, J=6.83 Hz), 4.34 (1H, d, J=16.60 Hz), 4.44 (1H, d, J=16.60 Hz), 4.69 (2H, dd, J=10.25, 2.93 Hz), 6.14 (1H, broad s), 6.84–6.92 (3H, m), 7.17–7.30 (5H, m).

Example 27

Synthesis of 2-[3-(2-indanyloxy)-4-methoxyphenyl]-2-methylmorpholin-5-one (Compound No. 27 of Table 1)

(1) 3-(2-indanyloxy)-4-methoxyacetophenone

According to the same procedure as used in Example 10(1), using the 3-(2-indanyloxy)-4-methoxybenzaldehyde produced in Example 6(1) instead of 3-cyclopentyloxy-4-methoxybenzaldehyde, 3-(2-indanyloxy)-4-methoxyacetophenone(yield 85.9%) was obtained as a light yellow solid.

¹H-NMR (400 MHz, CDCl₃) δ 2.57(3H, s), 3,25 (2H, dd, J=16.60, 3.42 Hz), 3.46 (2H, dd, J=16.60, 6.35 Hz), 3.90 (3H, s), 5.26 (1H, m), 6.98 (1H, d, J=8.30 Hz), 7.17–7.21 (2H, m), 7.22–7.25 (2H, m), 7.46–7.49 (2H, m), 9.87 (1H, s).

(2) 2-amino-1-[3-(2-indanyloxy)-4-methoxyphenyl]-1-methylethanol

According to the same procedure as used in Example 1(1), using 3-(2-indanyloxy)-4-methoxyacetophenone instead of 3,4-dimethoxybenzaldehyde, 2-amino-1-[3-(2-indanyloxy)-4-methoxyphenyl]-1-methylethanol was obtained as a light yellow solid.

¹H-NMR (400 MHz, CDCl₃) δ 1.47 (3H, s), 2.76–2.79 (1H, m), 3.04–3.07 (1H, m), 3.24 (2H, dd, J=16.60, 4.39 Hz), 3.38 (2H, dd, J=16.60, 6.34 Hz), 3.81 (3H, s), 5.23 (1H, m), 6.85 (1H, d, J=8.30 Hz), 6.96 (1H, dd, J=8.30, 1.95 Hz), 7.10 (1H, d, J=1.95 Hz), 7.16–7.19 (2H, m), 7.22–7.24 (2H, m).

(3) 2-[3-(2-indanyloxy)-4-methoxyphenyl]-2-methylmorpholin-5-one

According to the same procedure as used in Example 3(2), using 2-amino-1-[3-(2-indanyloxy)-4-methoxyphenyl]-1-methylethanol instead of 2-amino-1-(3-benzyloxy-4-methoxyphenyl)ethanol, the above-described compound (yield 54.9%) was obtained as a light brown solid.

1H-NMR (400 MHz, CDCl₃) δ 1.53 (3H, s), 3.22 (1H, dd, J=16.60, 2.93 Hz), 3.22 (1H, dd, J=16.60, 2.93 Hz), 3.36 (2H, dd, J=16.60, 6.83 Hz), 3.57 (1H, dd, J=12.70, 1.47 Hz), 3.81 (1H, dd, J=12.70, 3.91 Hz), 3.81 (3H, s), 3.98 (1H, d, J=17.09 Hz), 4.18 (1H, d, J=17.09 Hz), 5.21 (1H, m), 6.85 (1H, d, J=8.30 Hz), 6.93 (1H, dd, J=8.30, 1.95 Hz), 7.04 (1H, d, J=1.95 Hz), 7.16–7.20 (2H, m), 7.21–7.25 (2H, m), 7.29 (1H, broad s).

Example 28

Synthesis of 2.4-dimethyl-2-[3-(2-indanyloxy)-4-methoxyphenyl]morpholin-5-one (Compound No. 28 of Table 1)

According to the same procedure as used in Example 12, using the 2-[3-(2-indanyloxy)-4-methoxyphenyl]-2-methylmorpholin-5-one produced in Example 27 instead of 2-(3,4-dimethoxyphenyl)morpholin-5-one, the above-described compound (yield 92.9%) was obtained as a colorless solid.

¹H-NMR (400 MHz, CDCl₃) δ 1.54 (3H, s), 3.04 (3H, s), 3.21 (1H, dd, J=16.60, 3.90 Hz), 3.23 (1H, dd, J=16.60, 3.90 Hz), 3.35 (1H, dd, J=16.60, 2.44 Hz), 3.36 (1H, dd, J=16.60, 2.93 Hz), 3.61 (1H, d, J=12.70 Hz), 3.73 (1H, d, J=12.70 Hz), 3.82 (3H, s), 3.96 (1H, d, J=17.09 Hz), 4.18 (1H, d, J=17.09 Hz), 5.21 (1H, m), 6.85 (1H, s), 6.85 (1H, s), 7.00 (1H, s), 7.17–7.20 (2H, m), 7.23–7.26 (2H, m).

Example 29

Synthesis of 2-[4-methoxy-3-(5-phenylpentyloxy) phenyl]-4-methylmorpholin-5-one (Compound No. 29 of Table 1)

According to the same procedure as used in Example 12, using the 2-[4-methoxy-3-(5-phenylpentyloxy)phenyl] morpholin-5-one produced in Example 26 instead of 2-(3, 4-dimethoxyphenyl)morpholin-5-one, the above-described compound (yield 84.9%) was obtained as a light yellow oil.

¹H-NMR (400 MHz, CDCl₃) δ 1.50–1.56 (2H, m), 1.67–1.73 (2H, m), 1.86–1.91 (2H, m), 2.65 (2H, t, J=7.81 Hz), 3.02 (3H, s), 3.32 (1H, dd, J=12.21, 2.93 Hz), 3.55 (1H, dd, J=12.21, 10.25 Hz), 3.86 (3H, s), 4.02 (2H, t, J=6.83 Hz), 4.31 (1H, d, J=16.60 Hz), 4.41 (1H, d, J=16.60 Hz), 4.74 (1H, dd, J=10.25, 2.93 Hz), 6.84–6.92 (3H, m), 7.16–7.30 (5H, m).

Example 30

Synthesis of 2-[3-[2-(benzyloxy)ethoxy]-4-methoxyphenyl]morpholin-5-one (Compound No. 30 of Table 1)

(1) 3-[2-(benzyloxy)ethoxy]-4-methoxybenzaldehyde

According to the same procedure as used in Example 4(1), using 2-benzyloxyethanol instead of phenethyl alcohol, 3-[2-(benzyloxy)ethoxy]-4-methoxybenzaldehyde(yield 83.4%) was obtained as a light yellow oil.

¹H-NMR (400 MHz, CDCl₃) δ 3.89 (2H, t, J=4.88 Hz), 3.95 (3H, s), 4.27 (2H, t, J=4.88 Hz), 4.65 (2H, s), 6.97 (1H, d, J=8.30 Hz), 7.27–7.48 (7H, m), 9.83 (1H, s).

(2) 2-amino-1-[3-[2-(benzyloxy)ethoxy]-4-methoxyphenyl]ethanol

According to the same procedure as used in Example 1(1), using 3-[3-[2-(benzyloxy)ethoxy]-4-methoxybenzaldehyde instead of 3,4-dimethoxybenzaldehyde, 2-amino-1-[3-[2-(benzyloxy)ethoxy]-4-methoxyphenyl]ethanol was obtained as a black oil.

¹H-NMR (400 MHz, CDCl₃) δ 2.76 (1H, dd, J=12.70, 7.81 Hz), 2.94 (1H, dd, J=12.70, 3.91 Hz), 3.85 (3H, s), 3.87 (2H, t, J=5.37 Hz), 4.23 (2H, t, J=5.37 Hz), 4.53 (1H, dd, J=7.81, 3.91 Hz), 4.64 (2H, s), 6.85 (1H, d, J=8.30 Hz), 6.89 (1H, dd, J=8.30, 1.95 Hz), 6.97 (1H, d, J=1.95 Hz), 7.28–7.39 (5H, m).

(2) 2-[3-[2-(benzyloxy)ethoxy]-4-methoxyphenyl]-2-morpholin-5-one

According to the same procedure as used in Example 3(2), using 2-amino-1-[3-[2-(benzyloxy)ethoxy]-4-methoxyphenyl]ethanol instead of 2-amino-1-(3-benzyloxy-4-methoxyphenyl)ethanol, the above-described compound (yield 32.0%) was obtained as a light brown solid.

¹H-NMR (400 MHz, CDCl₃) δ 3.39 (1H, ddd, J=12.21, 3.42, 3.42 Hz), 3.47 (1H, dd, J=12.21, 10.25 Hz), 3.86 (3H, s), 3.87 (2H, t, J=5.37 Hz), 4.24 (2H, t, J=5.37 Hz), 4.31 (1H, d, J=17.09 Hz), 4.41 (1H, d, J=17.09 Hz), 4.63 (2H, s), 4.65 (1H, dd, J=10.25, 3.42 Hz), 6.61 (1H, broad), 6.86 (1H, d, J=8.30 Hz), 6.91 (1H, dd, J=8.30, 1.95 Hz), 6.99 (1H, d, J=1.95 Hz), 7.27–7.38 (5H, m).

Example 31

Synthesis of 2-(3-cyclopentyloxy-4-methoxyphenyl)-6,6-dimethylmorpholin-5-one (Compound No. 31 of Table 1)

(1) 2-(2-bromo-2-methylpropionamido)-1-(3-cyclopentyloxy-4-methoxyphenyl)ethanol According to the same procedure as used in Example 2(2), using 2-bromo-2-methylpropionyl bromide instead of chloroacetyl chloride, 2-(2-bromo-2-methylpropionamido)-1-(3-cyclopentyloxy-4-methoxyphenyl)ethanol was obtained.

(2) 2-(3-cyclopentyloxy-4-methoxyphenyl)-6,6-dimethylmorpholin-5-one

A crude product (1.03 g) of 2-(2-bromo-2-methylpropionamido)-1-(3-cyclopentyloxy-4-methoxyphenyl)ethanol and sodium hydride (60%) (0.23 g) were stirred in dry dimethylformamide (40 ml) at room temperature for one night. Water was added to the reaction solution obtained and the solution was extracted with ethyl acetate. Next, the extract was washed several times with water and was dried over anhydrous sodium sulfate, then the solvent was evaporated in vacuo to obtain a crude product. The crude product obtained was purified by flash chromatography (SiO₂: eluted with gradient of range from 33% ethyl acetate/hexane to 75% ethyl acetate/hexane) to obtain the above-described compound 0.17 g (yield 21.1%) as a light yellow solid.

¹H-NMR (400 MHz, CDCl₃) δ 1.30 (3H, s), 1.36 (3H, s), 1.61–1.64 (2H, m), 1.85–2.05 (6H, m), 3.55 (1H, dd, J=14.65, 6.84 Hz), 3.66 (1H, dd, J=14.65, 2.93 Hz), 3.84 (3H, s), 4.45 (1H, broad), 4.79 (1H, m), 4.93 (1H, m), 6.84 (1H, d, J=8.30 Hz), 6.90–6.94 (2H, m).

Example 32

Synthesis of 2-[3-[2-(4-fluorophenyl)ethoxy]-4-methoxyphenyl]morpholin-5-one (Compound No. 32 of Table 1)

(1) 3-[2-(4-fluorophenyl)ethoxy]-4-methoxybenzaldehyde

According to the same procedure as used in Example 4(1), using 2-(4-fluorophenyl)ethanol instead of phenethyl alcohol, 3-[2-(4-fluorophenyl)ethoxy]-4-methoxybenzaldehyde(yield 91.6%) was obtained as a light yellow oil.

¹H-NMR (400 MHz, CDCl₃) δ 3.15 (2H, t, J=7.32 Hz), 3.96 (3H, s), 4.25 (2H, t, J=7.32 Hz), 6.98 (1H, d, J=8.30 Hz), 6.98–7.03 (2H, m), 7.24–7.28 (2H, m), 7.39 (1H, d, J=1.47 Hz), 7.46 (1H, dd, J=8.30, 1.47 Hz), 9.83 (1H, s).

(2) 2-amino-1-[3-[2-(4-fluorophenyl)ethoxy]-4-methoxyphenyl]ethanol

According to the same procedure as used in Example 1(1), using 3-[3-[2-(4-fluorophenyl)ethoxy]-4-methoxybenzaldehyde instead of 3,4-dimethoxybenzaldehyde, 2-amino-1-[3-[2-(4-fluorophenyl)ethoxy]-4-methoxyphenyl]ethanol was obtained as an orange solid.

¹H-NMR (400 MHz, CDCl₃) δ 1.24 (2H, broad), 2.76 (1H, dd, J=12.70, 7.82 Hz), 2.96 (1H, dd, J=12.70, 3.90 Hz), 3.12 (2H, t, J=7.32 Hz), 3.85 (3H, s), 4.19 (2H, t, J=7.32 Hz), 4.54 (1H, dd, J=7.82, 3.90 Hz), 6.84–6.90 (3H, m), 6.97–7.01 (2H, m), 7.23–7.27 (2H, m).

(3) 2-[3-[2-(4-fluorophenyl)ethoxy]-4-methoxyphenyl]-2-methylmorpholin-5-one

According to the same procedure as used in Example 3(2), using 2-amino-1-[3-[2-(4-fluorophenyl)ethoxy]-4-methoxyphenyl]ethanol instead of 2-amino-1-(3-benzyloxy-4-methoxyphenyl)ethanol, the above-described compound (yield 51.5%) was obtained as a light brown solid.

¹H-NMR (400 MHz, CDCl₃) δ 3.13 (2H, t, J=7.32 Hz), 3.44 (1H, ddd, J=12.21, 3.42, 3.42 Hz), 3.50 (1H, dd, J=12.21, 10.25 Hz), 3.86 (3H, s), 4.19 (2H, t, J=7.32 Hz), 4.32 (1H, d, J=17.09 Hz), 4.42 (1H, d, J=17.09 Hz), 4.67 (1H, dd, J=10.25, 3.42 Hz), 6.40 (1H, broad), 6.85–6.90 (3H, m), 6.98–7.02 (2H, m), 7.24–7.27 (2H, m).

Example 33

Synthesis of 2-[4-methoxy-3-(trans-4-phenylcyclohexyloxy)phenyl]morpholin-5-one (Compound No. 33 of Table 1)

(1) 4-methoxy-3-(trans-4-phenylcyclohexyloxy)benzaldehyde

According to the same procedure as used in Example 4(1), using cis-1-hydroxy-4-phenylcyclohexane instead of phenethyl alcohol, 4-methoxy-3-(trans-4-phenylcyclohexyloxy)benzaldehyde (yield 37.5%) was obtained as a colorless solid.

¹H-NMR (400 MHz, CDCl₃) δ 1.59–1.76 (4H, m), 2.01–2.04 (2H, m), 2.30–2.33 (2H, m), 2.60 (1H, m), 3.96 (3H, s), 4.35–4.41 (1H, m), 7.00 (1H, d, J=7.81 Hz), 7.19–7.33 (5H, m), 7.46–7.48 (2H, m), 9.86 (1H, s).

(2) 2-amino-1-[4-methoxy-3-(trans-4-phenylcyclohexyloxy)phenyl]ethanol

According to the same procedure as used in Example 1(1), using 4-methoxy-3-(trans-4-phenylcyclohexyloxy)benzaldehyde instead of 3,4-dimethoxybenzaldehyde, 2-amino-1-[4-methoxy-3-(trans-4-phenylcyclohexyloxy)phenyl]ethanol was obtained as a light yellow oil.

¹H-NMR (400 MHz, CDCl₃) δ 1.19 (2H, broad), 1.54–1.74 (4H, m), 1.98–2.01 (2H, m), 2.27–2.30 (2H, m), 2.58 (11H, dddd, J=11.72, 11.72, 3.42, 3.42 Hz), 2.81 (1H, dd, J=12.70, 7.81 Hz), 2.99 (1H, dd, J=12.70, 3.91 Hz), 3.17 (11H, broad), 3.86 (3H, s), 4.25 (1H, m, J=4.39 Hz), 4.57 (11H, dd, J=7.81, 3.90 Hz), 6.87 (1H, d, J=8.30 Hz), 6.92 (1H, dd, J=8.30, 1.96 Hz), 7.00 (1H, d, J=1.96 Hz), 7.18–7.23 (3H, m), 7.28–7.32 (2H, m).

(3) 2-[4-methoxy-3-(trans-4-phenylcyclohexyloxy)phenyl]morpholin-5-one

According to the same procedure as used in Example 3(2), using 2-amino-1-[4-methoxy-3-(trans-4-phenylcyclohexyloxy)phenyl]ethanol instead of 2-amino-1-(3-benzyloxy-4-methoxyphenyl)ethanol, the above-described compound (yield 57.5%) was obtained as a light brown oil.

$^1$H-NMR (400 MHz, CDCl$_3$) δ 1.54–1.74 (4H, m), 1.99–2.02 (2H, m), 2.26–2.29 (2H, m), 2.58 (1H, m), 3.48 (1H, ddd, J=12.21, 3.41, 3.41 Hz), 3.57 (1H, dd, J=12.21, 10.25 Hz), 3.87 (3H, s), 4.23–4.28 (1H, m), 4.35 (1H, d, J=17.09 Hz), 4.45 (1H, d, J=17.09 Hz), 4.70 (1H, dd, J=10.25, 3.41 Hz), 6.13 (1H, broad), 6.89 (11H, d, J=8.30 Hz), 6.94 (1H, dd, J=8.30, 1.47 Hz), 7.01 (1H, d, J=1.47 Hz), 7.18–7.32 (5H, m).

Example 34

Synthesis of 2-[4-methoxy-3-[(1-phenylcyclopropyl)methoxy]phenyl]morpholin-5-one (Compound No. 34 of Table 1)

(1) 4-methoxy-3-[(1-phenylcyclopropyl)methoxy]benzaldehyde

According to the same procedure as used in Example 4(1), using 1-phenylcyclopropylmethanol instead of phenethyl alcohol, 4-methoxy-3-[(1-phenylcyclopropyl)methoxy]benzaldehyde(yield 74.8%) was obtained as a yellow oil.

$^1$H-NMR (400 MHz, CDCl$_3$) δ 1.00–1.02 (2H, m), 1.04–1.07 (2H, m), 3.90 (3H, s), 4.13 (2H, s), 6.93 (1H, d, J=7.81 Hz), 7.19–7.23 (1H, m), 7.28–7.31 (3H, m), 7.41–7.45 (3H, m), 9.79 (1H, s).

(2) 2-[4-methoxy-3-[(1-phenylcyclopropyl)methoxy]phenyl]morpholin-5-one

According to the same procedure as used in Example 3(1) to (2), using 4-methoxy-3-[(1-phenylcyclopropyl)methoxy]benzaldehyde instead of 3-benzyloxy-4-methoxybenzaldehyde, the above-described compound (yield 22.1%) was obtained as a yellow oil.

H-NMR (400 MHz, CDCl$_3$) δ 0.96–1.00 (2H, m), 1.04–1.06 (2H, m), 3.39 (1H, ddd, J=12.21, 3.42, 3.42 Hz), 3.47 (1H, dd, J=12.21, 10.25 Hz), 3.80 (3H, s), 4.10 (2H, s), 4.30 (1H, d, J=17.09 Hz), 4.40 (1H, d, J=17.09 Hz), 4.62 (1H, dd, J=10.25, 3.42 Hz), 6.56 (1H, broad), 6.80 (1H, d, J=1.95 Hz), 6.83 (1H, d, J=8.30 Hz), 6.87 (1H, dd, J=8.30, 1.95 Hz), 7.20 (1H, t, J=7.33 Hz), 7.29 (2H, t, J=7.33 Hz), 7.44 (2H, d, J=7.33 Hz).

Example 35

Synthesis of 2-[3-[(1-methylcyclopropyl)methoxy]-4-methoxyphenyl]morpholin-5-one (Compound No. 35 of Table 1)

(1) 3-[(1-methylcyclopropyl)methoxy]-4-methoxybenzaldehyde

According to the same procedure as used in Example 4(1), using 1-methylcyclopropylmethanol instead of phenethyl alcohol, 3-[1-(methylcyclopropyl)methoxy]-4-methoxybenzaldehyde(yield 65.0%) was obtained as a yellow oil.

$^1$H-NMR (400 MHz, CDCl$_3$) δ 0.45–0.47 (2H, m), 0.56–0.57 (2H, m), 1.27 (3H, s), 3.84 (2H, s), 3.95 (3H, s), 6.97 (1H, d, J=8.30 Hz), 7.37 (1H, broad), 7.45 (1H, dd, J=8.30, 1.46 Hz), 9.83 (1H, s).

(2) 2-amino-1-[3-[(1-methylcyclopropyl)methoxy]-4-methoxyphenyl]ethanol

According to the same procedure as used in Example 1(1), using 3-[(1-methylcyclopropyl)methoxy]-4-methoxybenzaldehyde instead of 3,4-dimethoxybenzaldehyde, 2-amino-1-[3-[(1-methylcyclopropyl)methoxy]-4–7methoxyphenyl]ethanol was obtained as a peach colored solid.

$^1$H-NMR (400 MHz, CDCl$_3$) 0.39–0.42 (2H, m), 0.43–0.54 (2H, m), 1.23 (3H, s), 2.80–2.86 (1H, m), 2.98–3.01 (1H, m), 3.74 (2H, s), 3.82 (3H, s), 4.60 (1H, m), 6.79–6.88 (3H, m).

(3) 2-[3-[(1-methylcyclopropyl)methoxy]-4-methoxyphenyl]morpholin-5-one

According to the same procedure as used in Example 3(2), using 2-amino-1-[3-[(1-methylcyclopropyl)methoxy]-4-methoxyphenyl]ethanol instead of 2-amino-1-(3-benzyloxy-4-methoxyphenyl)ethanol, the above-described compound (yield 20.8%) was obtained as a light brown solid.

$^1$H-NMR (400 MHz, CDCl$_3$) δ 0.42–0.45 (2H, m), 0.54–0.56 (2H, m), 1.26 (3H, s), 3.45 (1H, ddd, J=12.20, 3.90, 3.90 Hz), 3.53 (1H, dd, J=12.20, 10.26 Hz), 3.79 (2H, s), 3.86 (3H, s), 4.33 (1H, d, J=17.09 Hz), 4.42 (1H, d, J=17.09 Hz), 4.67 (1H, dd, J=10.26, 3.90 Hz), 6.85–6.91 (4H, m).

Example 36

Synthesis of 2-(3-cyclopentylmethoxy-4-methoxyphenyl)morpholin-5-one (Compound No. 36 of Table 1)

(1) 3-cyclopentylmethoxy-4-methoxybenzaldehyde

According to the same procedure as used in Example 4(1), using cyclopentylmethanol instead of phenethyl alcohol, 3-cyclopentylmethoxy-4-methoxybenzaldehyde (yield 80.6%) was obtained as a yellow oil.

$^1$H-NMR (400 MHz, CDCl$_3$) δ 1.36–1.42 (2H, m), 1.56–1.66 (4H, m), 1.83–1.92 (2H, m), 2.46 (1H, m), 3.94 (2H, d, J=7.32 Hz), 3.95 (3H, s), 6.97 (1H, d, J=7.81 Hz), 7.41 (1H, d, J=1.95 Hz), 7.44 (1H, dd, J=7.81, 1.95 Hz), 9.84 (1H, s).

(2) 2-amino-1-(3-cyclopentylmethoxy-4-methoxyphenyl)ethanol

According to the same procedure as used in Example 1(1), using 3-cyclopentylmethoxy-4-methoxybenzaldehyde instead of 3,4-dimethoxybenzaldehyde, 2-amino-1-(3-cyclopentylmethoxy-4-methoxyphenyl)ethanol was obtained as a light yellow solid.

$^1$H-NMR (400 MHz, CDCl$_3$) δ 1.36–1.39 (2H, m), 1.58–1.64 (4H, m), 1.84–1.87 (2H, m), 2.44 (1H, m), 2.81 (1H, dd, J=12.70, 7.82 Hz), 2.98 (1H, dd, J=12.70, 3.90 Hz), 3.85 (3H, s), 3.88 (2H, d, J=7.32 Hz), 4.56 (1H, dd, J=7.82, 3.90 Hz), 6.85 (2H, s), 6.93 (1H, s).

(3) 2-(3-cyclopentylmethoxy-4-methoxyphenyl)morpholin-5-one

According to the same procedure as used in Example 3(2), using 2-amino-1-(3-cyclopentylmethoxy-4-methoxyphenyl)ethanol instead of 2-amino-1-(3-benzyloxy-4-methoxyphenyl)ethanol, the above-described compound (yield 25.2%) was obtained as a light yellow solid.

$^1$H-NMR (400 MHz, CDCl$_3$) δ 1.35–1.39 (2H, m), 1.56–1.67 (4H, m), 1.83–1.90 (2H, m), 2.44 (1H, m, J=7.33 Hz), 3.47 (1H, ddd, J=12.21, 3.42, 3.42 Hz), 3.57 (1H, dd, J=12.21, 10.25 Hz), 3.86 (3H, s), 3.89 (2H, d, J=7.33 Hz), 4.35 (1H, d, J=17.09 Hz), 4.46 (1H, d, J=17.09 Hz), 4.70 (1H, dd, J=10.25, 3.42 Hz), 6.22 (1H, broad), 6.86 (1H, d, J=8.30 Hz), 6.87 (1H, dd, J=8.30, 1.95 Hz), 6.94 (1H, d, J=1.95 Hz).

Example 37

Synthesis of 2-[4-methoxy-3-[2-(1-naphthyl)ethoxy]phenyl]morpholin-5-one (Compound No. 37 of Table 1)

(1) 4-methoxy-3-[2-(1-naphthyl)ethoxy]benzaldehyde

According to the same procedure as used in Example 4(1), using 2-(1-naphthyl)ethanol instead of phenethyl alcohol, 4-methoxy-3-[2-(1-naphthyl)ethoxy] benzaldehyde(yield 54.1%) was obtained as a colorless solid.

$^1$H-NMR (400 MHz, CDCl$_3$) δ 3.67 (2H, t, J=7.81 Hz), 3.96 (3H, s), 4.41 (2H, t, J=7.81 Hz), 6.98 (1H, d, J=8.30 Hz), 7.37 (1H, d, J=1.47 Hz), 7.41–7.46 (2H, m), 7.48 (1H, dd, J=7.82, 0.97 Hz), 7.51 (1H, dd, J=3.42, 1.47 Hz), 7.55 (1H, dd, J=6.84, 1.47 Hz), 7.77 (1H, dd, J=6.84, 2.45 Hz), 7.87 (1H, dd, J=8.30, 0.97 Hz), 8.11 (1H, d, J=8.30 Hz), 9.80 (1H, s).

(2) 2-amino-1-[4-methoxy-3-[2-(1-naphthyl)ethoxy]phenyl]ethanol

According to the same procedure as used in Example 1(1), using 4-methoxy-3-[2-(1-naphthyl)ethoxy]benzaldehyde instead of 3,4-dimethoxybenzaldehyde, 2-amino-1-[4-methoxy-3-[2-(1-naphthyl)ethoxy]phenyl]ethanol was obtained as a light yellow oil.

$^1$H-NMR (400 MHz, CDCl$_3$) δ 1.13 (2H, broad), 2.73 (1H, dd, J=12.21, 7.81 Hz), 2.93 (1H, dd, J=12.21, 3.90 Hz), 3.13 (1H, broad), 3.66 (2H, t, J=7.81 Hz), 3.87 (3H, s), 4.35 (2H, t, J=7.81 Hz), 4.50 (1H, m), 6.84–6.91 (3H, m), 7.40–7.55 (4H, m), 7.77 (1H, dd, J=9.28, 1.95 Hz), 7.87 (1H, d, J=7.33 Hz), 8.12 (1H, d, J=7.81 Hz).

(3) 2-[4-methoxy-3-[2-(1-naphthyl)ethoxy]phenyl]morpholin-5-one

According to the same procedure as used in Example 3(2), using 2-amino-1-[4-methoxy-3-[2-(1-naphthyl)ethoxy]phenyl]ethanol instead of 2-amino-1-(3-benzyloxy-4-methoxyphenyl)ethanol, the above-described compound (yield 53.2%) was obtained as a colorless solid.

$^1$H-NMR (400 MHz, CDCl$_3$) δ 3.39 (1H, ddd, J=11.72, 3.42, 3.42 Hz), 3.47 (1H, dd, J=11.72, 10.25 Hz), 3.67 (2H, t, J=7.81 Hz), 3.89 (3H, s), 4.29 (1H, d, J=17.09 Hz), 4.35 (2H, t, J=7.81 Hz), 4.39 (1H, d, J=17.09 Hz), 4.63 (1H, dd, J=10.25, 3.42 Hz), 6.06 (1H, broad), 6.87–6.88 (3H, m), 7.41–7.46 (2H, m), 7.48–7.55 (2H, m), 7.78 (1H, dd, J=6.35, 2.45 Hz), 7.87–7.89 (1H, m), 8.12 (1H, d, J=7.81 Hz).

Example 38

Synthesis of 2-(3-cyclobutylmethoxy-4-methoxyphenyl)morpholin-5-one (Compound No. 38 of Table 1)
(1) 3-cyclobutylmethoxy-4-methoxybenzaldehyde According to the same procedure as used in Example 4(1), using cyclobutylmethanol instead of phenethyl alcohol, 3-cyclobutylmethoxy-4-methoxybenzaldehyde (yield 77.1%) was obtained as a light yellow oil.

$^1$H-NMR (400 MHz, CDCl$_3$) δ 1.84–2.01 (4H, m), 2.14–2.22 (2H, m), 2.86 (1H, m), 3.94 (3H, s), 4.06 (2H, d, J=6.83 Hz), 6.97 (1H, d, J=8.30 Hz), 7.41 (1H, d, J=1.95 Hz), 7.44 (1H, dd, J=8.30, 1.95 Hz), 9.85 (1H, s).

(2) 2-amino-1-(3-cyclobutylmethoxy-4-methoxyphenyl)ethanol

According to the same procedure as used in Example 1(1), using 3-cyclobutylmethoxy-4-methoxybenzaldehyde instead of 3,4-dimethoxybenzaldehyde, 2-amino-1-(3-cyclobutylmethoxy-4-methoxyphenyl)ethanol was obtained as a yellow solid.

$^1$H-NMR (400 MHz, CDCl$_3$) δ 1.18 (2H, broad), 1.83–1.99 (4H, m), 2.12–2.19 (2H, m), 2.78–2.87 (2H, m), 2.98 (1H, dd, J=12.70, 3.90 Hz), 3.15 (1H, broad), 3.84 (3H, s), 4.01 (2H, d, J=6.84 Hz), 4.56 (1H, dd, J=7.82, 3.90 Hz), 6.84 (1H, d, J=8.30 Hz), 6.87 (1H, dd, J=8.30, 1.95 Hz), 6.93 (1H, d, J=1.95 Hz).

(3) 2-(3-cyclobutylmethoxy-4-methoxyphenyl)morpholin-5-one

According to the same procedure as used in Example 3(2), using 2-amino-1-(3-cyclobutylmethoxy-4-methoxyphenyl)ethanol instead of 2-amino-1-(3-benzyloxy-4-methoxyphenyl)ethanol, the above-described compound (yield 48.8%) was obtained as a colorless solid.

$^1$H-NMR (400 MHz, CDCl$_3$) δ 1.82–2.01 (4H, m), 2.13–2.21 (2H, m), 2.84 (1H, m), 3.47 (1H, ddd, J=12.21, 3.41, 3.41 Hz), 3.57 (1H, dd, J=12.21, 10.25 Hz), 3.86 (3H, s), 4.01 (2H, d, J=7.33 Hz), 4.35 (1H, d, J=16.60 Hz), 4.45 (1H, d, J=16.60 Hz), 4.70 (1H, dd, J=10.25, 3.41 Hz), 6.23 (1H, broad), 6.85 (1H, d, J=8.30 Hz), 6.89 (1H, dd, J=8.30, 1.95 Hz), 6.94 (1H, d, J=1.95 Hz).

Example 39

Synthesis of 2-[3-(2-methylpropoxy)-4-methoxyohenyl]morpholin-5-one (Compound No. 39 of Table 1)
(1) 3-(2-methylpropoxy)-4-methoxybenzaldehyde According to the same procedure as used in Example 4(1), using isobutanol instead of phenethyl alcohol, 3-(2-methylpropoxy)-4-methoxybenzaldehyde (yield 75.8%) was obtained as a yellow oil.

$^1$H-NMR (400 MHz, CDCl$_3$) δ 1.05 (6H, d, J=6.83 Hz), 2.19 (1H, m, J=6.83 Hz), 3.83 (2H, d, J=6.83 Hz), 3.95 (3H, s), 6.97 (1H, d, J=7.81 Hz), 7.40 (1H, d, J=1.46 Hz), 7.44 (1H, dd, J=7.81, 1.46 Hz), 9.84 (1H, s).

(2) 2-amino-1-[3-(2-methylpropoxy)-4-methoxyphenyl]ethanol

According to the same procedure as used in Example 1(1), using 3-(2-methylpropoxy)-4-methoxybenzaldehyde instead of 3,4-dimethoxybenzaldehyde, 2-amino-1-[3-(2-methylpropoxy)-4-methoxyphenyl]ethanol was obtained as a light yellow solid.

$^1$H-NMR (400 MHz, CDCl$_3$) δ 1.03 (6H, d, J=6.83 Hz), 1.18 (2H, broad), 2.17 (1H, m), 2.81 (1H, dd, J=12.69, 7.81 Hz), 2.98 (1H, dd, J=12.69, 4.39 Hz), 3.17 (1H, broad), 3.78 (2H, d, J=6.83 Hz), 3.85 (3H, s), 4.56 (1H, dd, J=7.81, 4.39 Hz), 6.85–6.92 (3H, m).

(3) 2-[3-(2-methylpropoxy)-4-methoxyphenyl]morpholin-5-one

According to the same procedure as used in Example 3(2), using 2-amino-1-[3-(2-methylpropoxy)-4-methoxyphenyl]ethanol instead of 2-amino-1-(3-benzyloxy-4-methoxyphenyl)ethanol, the above-described compound (yield 50.7%) was obtained as a colorless solid.

$^1$H-NMR (400 MHz, CDCl$_3$) δ 1.04 (6H, d, J=6.83 Hz), 2.17 (1H, m, J=6.83 Hz), 3.47 (1H, ddd, J=12.21, 3.42, 3.42 Hz), 3.56 (1H, dd, J=12.21, 10.25 Hz), 3.78 (2H, d, J=6.83 Hz), 3.86 (3H, s), 4.34 (1H, d, J=17.09 Hz), 4.44 (1H, d, J=17.09 Hz), 4.69 (1H, dd, J=10.25, 3.42 Hz), 6.36 (1H, broad), 6.86 (1H, d, J=8.30 Hz), 6.89 (1H, dd, J=8.30, 1.95 Hz), 6.93 (1H, d, J=1.95 Hz).

Example 40

Synthesis of 4-ethyl-2-[3-(2-indanyloxy)-4-methoxyphenyl]morpholin-5-one (Compound No. 40 of Table 1)

According to the same procedure as used in Example 21, using ethyl iodide instead of methyl iodide, the above-described compound (yield 99.0%) was obtained as a light yellow-green solid.

$^1$H-NMR (400 MHz, CDCl$_3$) δ 1.20 (3H, t, J=7.33 Hz), 3.24 (2H, dd, J=16.60, 3.91 Hz), 3.32 (1H, dd, J=12.20, 3.42 Hz), 3.36–3.46 (3H, m), 3.52–3.59 (1H, m), 3.54 (1H, dd, J=12.20, 10.25 Hz), 3.82 (3H, s), 4.31 (1H, d, J=16.60 Hz), 4.42 (1H, d, J=16.60 Hz), 4.74 (1H, dd, J=10.25, 3.42 Hz), 5.22 (1H, m), 6.88 (1H, d, J=8.30 Hz), 6.94 (1H, dd, J=8.30, 1.96 Hz), 7.00 (1H, d, J=1.96 Hz), 7.17–7.20 (2H, m), 7.22–7.25 (2H, m).

Example 41

Synthesis of 2-[3-[2-(4-fluorophenyl)ethoxy]-4-methoxyphenyl]-4-methylmorpholin-5-one (Compound No. 41 of Table 1)

According to the same procedure as used in Example 12, using the 2-[3-[2-(4-fluorophenyl)ethoxy]-4-methoxyphenyl]morpholin-5-one produced in Example 32 instead of 2-(3,4-dimethoxyphenyl)morpholin-5-one, the above-described compound (yield 92.5%) was obtained as a light yellow oil.

$^1$H-NMR (400 MHz, CDCl$_3$) δ 3.00 (3H, s), 3.13 (2H, t, J=7.32 Hz), 3.29 (1H, dd, J=12.21, 3.42 Hz), 3.52 (1H, dd, J=12.21, 10.74 Hz), 3.86 (3H, s), 4.20 (2H, t, J=7.32 Hz), 4.29 (1H, d, J=16.60 Hz), 4.39 (1H, d, J=16.60 Hz), 4.72 (1H, dd, J=10.74, 3.42 Hz), 6.86–6.91 (3H, m), 6.98–7.02 (2H, m), 7.24–7.27 (2H, m).

Example 42

Synthesis of 2-[3-[(1-phenylcyclopropyl)methoxy]-4-methoxyphenyl]-4-methylmorpholin-5-one (Compound No. 42 of Table 1)

According to the same procedure as used in Example 12, using the 2-[3-[(1-phenylcyclopropyl)methoxy]-4-methoxyphenyl]morpholin-5-one produced in Example 34 instead of 2-(3,4-dimethoxyphenyl)morpholin-5-one, the above-described compound (yield 100%) was obtained as a light yellow solid.

$^1$H-NMR (400 MHz, CDCl$_3$) δ 0.98–1.00 (2H, m), 1.04–1.07 (2H, m), 3.00 (3H, s), 3.25 (1H, dd, J=12.70, 3.42 Hz), 3.47 (1H, dd, J=12.70, 10.74 Hz), 3.80 (3H, s), 4.11 (2H, s), 4.28 (1H, d, J=16.60 Hz), 4.38 (1H, d, J=16.60 Hz), 4.67 (1H, dd, J=10.74, 3.42 Hz), 6.79 (1H, d, J=1.47 Hz), 6.83 (1H, d, J=8.30 Hz), 6.86 (1H, dd, J=8.30, 1.47 Hz), 7.19–7.22 (1H, m), 7.28–7.31 (2H, m), 7.43–7.45 (2H, m).

Example 43

Synthesis of 2-13-[(1-methylcyclopropyl)methoxy]-4-methoxyphenyl]-4-methylmorpholin-5-one (Compound No. 43 of Table 1)

According to the same procedure as used in Example 12, using the 2-[3-[(1-methylcyclopropyl)methoxy]-4-methoxyphenyl]morpholin-5-one produced in Example 35 instead of 2-(3,4-dimethoxyphenyl)morpholin-5-one, the above-described compound (yield 100%) was obtained as a light yellow oil.

$^1$H-NMR (400 MHz, CDCl$_3$) δ 0.42–0.45 (2H, m), 0.54–0.56 (2H, m), 1.27 (3H, s), 3.01 (3H, s), 3.31 (1H, dd, J=12.20, 2.93 Hz), 3.55 (1H, dd, J=12.20, 10.25 Hz), 3.79 (2H, s), 3.86 (3H, s), 4.30 (1H, d, J=16.60 Hz), 4.40 (1H, d, J=16.60 Hz), 4.73 (1H, dd, J=10.25, 2.93 Hz), 6.86 (1H, d, J=8.30 Hz), 6.89 (1H, dd, J=8.30, 1.95 Hz), 6.92 (1H, d, J=1.95 Hz).

Example 44

Synthesis of 2-(3-cyclopentylmethoxy-4-methoxyphenyl)-4-methylmorpholin-5-one (Compound No. 44 of Table 1)

According to the same procedure as used in Example 12, using the 2-(3-cyclopentylmethoxy-4-methoxyphenyl)morpholin-5-one produced in Example 36 instead of 2-(3,4-dimethoxyphenyl)morpholin-5-one, the above-described compound (yield 100%) was obtained as a yellow oil.

$^1$H-NMR (400 MHz, CDCl$_3$) δ 1.32–1.42 (2H, m), 1.54–1.68 (4H, m), 1.83–1.92 (2H, m), 2.44 (1H, m), 3.02 (3H, s), 3.32 (1H, dd, J=12.21, 2.93 Hz), 3.56 (1H, dd, J=12.21, 10.75 Hz), 3.86 (3H, s), 3.89 (2H, d, J=7.33 Hz), 4.31 (1H, d, J=16.60 Hz), 4.41 (1H, d, J=16.60 Hz), 4.75 (1H, dd, J=10.75, 2.93 Hz), 6.85 (1H, d, J=8.30 Hz), 6.88 (1H, dd, J=8.30, 1.46 Hz), 6.94 (1H, d, J=1.46 Hz).

Example 45

Synthesis of 2-[4-methoxy-3-(trans-4-phenylcyclohexyloxy)phenyl]-4-methylmorpholin-5-one (Compound No. 45 of Table 1)

According to the same procedure as used in Example 12, using the 2-[4-methoxy-3-(trans-4-phenylcyclohexyloxy)phenyl]morpholin-5-one produced in Example 33 instead of 2-(3,4-dimethoxyphenyl)morpholin-5-one, the above-described compound (yield 85.1%) was obtained as a colorless solid.

$^1$H-NMR (400 MHz, CDCl$_3$) δ 1.55–1.74 (4H, m), 2.00–2.03 (2H, m), 2.27–2.29 (2H, m), 2.56–2.61 (1H, m), 3.02 (3H, s), 3.33 (1H, dd, J=12.21, 3.41 Hz), 3.56 (1H, dd, J=12.21, 10.75 Hz), 3.87 (3H, s), 4.23–4.28 (1H, m), 4.32 (1H, d, J=16.60 Hz), 4.42 (1H, d, J=16.60 Hz), 4.75 (1H, dd, J=10.74, 3.41 Hz), 6.89 (1H, d, J=8.30 Hz), 6.93 (1H, dd, J=8.30, 1.95 Hz), 7.01 (1H, d, J=1.95 Hz), 7.18–7.32 (5H, m).

Example 46

Synthesis of 2-[4-methoxy-3-(2-benzyloxyethoxy)phenyl]-4-methylmorpholin-5-one (Compound No. 46 of Table 1)

According to the same procedure as used in Example 12, using the 2-[4-methoxy-3-(2-benzyloxyethoxy)phenyl]morpholin-5-one produced in Example 30 instead of 2-(3,4-dimethoxyphenyl)morpholin-5-one, the above-described compound (yield 93.1%) was obtained as a light brown solid.

$^1$H-NMR (400 MHz, CDCl$_3$) δ 2.99 (3H, s), 3.27 (1H, dd, J=12.21, 3.42 Hz), 3.50 (1H, dd, J=12.21, 10.74 Hz), 3.87 (3H, s), 3.88 (2H, t, J=4.88 Hz), 4.24 (2H, t, J=4.88 Hz), 4.29 (1H, d, J=16.60 Hz), 4.39 (1H, d, J=16.60 Hz), 4.64 (2H, s), 4.71 (1H, dd, J=10.74, 3.42 Hz), 6.86 (1H, d, J=8.30 Hz), 6.91 (1H, dd, J=8.30, 1.95 Hz), 7.00 (1H, d, J=1.95 Hz), 7.28–7.40 (5H, m).

Example 47

Synthesis of 2-[4-methoxy-3-[2-(1-naphthyl)ethoxy]phenyl]-4-methylmorpholin-5-one (Compound No. 47 of Table 1)

According to the same procedure as used in Example 12, using the 2-[4-methoxy-3-[2-(1-naphthyl)ethoxy]phenyl]morpholin-5-one produced in Example 37 instead of 2-(3,4-dimethoxyphenyl)morpholin-5-one, the above-described compound (yield 88.2%) was obtained as a colorless solid.

$^1$H-NMR (400 MHz, CDCl$_3$) δ 2.98 (3H, s), 3.25 (1H, dd, J=12.20, 2.93 Hz), 3.47 (1H, dd, J=12.20, 10.74 Hz), 3.67

(2H, t, J=7.81 Hz), 3.89 (3H, s), 4.26 (1H, d, J=16.60 Hz), 4.35 (2H, t, J=7.81 Hz), 4.36 (1H, d, J=16.60 Hz), 4.68 (1H, dd, J=10.74, 2.93 Hz), 6.86–6.88 (3H, m), 7.41–7.45 (2H, m), 7.48–7.55 (2H, m), 7.77 (1H, dd, J=6.83, 2.93 Hz), 7.88 (1H, dd, J=7.82, 1.46 Hz), 8.12 (1H, d, J=8.30 Hz).

Example 48

Synthesis of 2-(3-cyclobutylmethoxy-4-methoxyphenyl)-4-methylmorpholin-5-one (Compound No. 48 of Table 1)

According to the same procedure as used in Example 12, using the 2-(3-cyclobutylmethoxy-4-methoxyphenyl) morpholin-5-one produced in Example 38 instead of 2-(3,4-dimethoxyphenyl)morpholin-5-one, the above-described compound (yield 99.9%) was obtained as a light yellow oil.

$^1$H-NMR (400 MHz, CDCl$_3$) δ 1.82–2.01 (4H, m), 2.13–2.21 (2H, m), 2.84 (1H, m), 3.02 (3H, s), 3.32 (1H, dd, J=12.21, 3.42 Hz), 3.56 (1H, dd, J=12.21, 10.74 Hz), 3.85 (3H, s), 4.01 (2H, d, J=6.84 Hz), 4.31 (1H, d, J=16.60 Hz), 4.42 (1H, d, J=16.60 Hz), 4.75 (1H, dd, J=10.74, 3.42 Hz), 6.85 (1H, d, J=8.30 Hz), 6.89 (1H, dd, J=8.30, 1.95 Hz), 6.94 (1H, d, J=1.95 Hz).

Example 49

Synthesis of 2-[3-(2-methylpropoxy)-4-methoxyphenyl]-4-methylmorpholin-5-one (Compound No. 49 of Table 1)

According to the same procedure as used in Example 12, using the 2-[3-(2-methylpropoxy)-4-methoxyphenyl] morpholin-5-one produced in Example 39 instead of 2-(3,4-dimethoxyphenyl)morpholin-5-one, the above-described compound (yield 99.8%) was obtained as a light yellow oil.

$^1$H-NMR (400 MHz, CDCl$_3$) δ 1.04 (6H, d, J=6.84 Hz), 2.17 (1H, m, J=6.84 Hz), 3.02 (3H, s), 3.32 (1H, dd, J=12.21, 3.42 Hz), 3.56 (1H, dd, J=12.21, 10.74 Hz), 3.78 (2H, d, J=6.84 Hz), 3.86 (3H, s), 4.31 (1H, d, J=16.60 Hz), 4.41 (11H, d, J=16.60 Hz), 4.75 (1H, dd, J=10.74, 3.42 Hz), 6.85–6.89 (2H, m), 6.93 (1H, d, J=1.47 Hz).

Example 50

Synthesis of 2-[3-[2-(2-indanyl)ethoxy]-4-methoxyphenyl]morpholin-5-one (Compound No. 50 of Table 1)

(1) 3-[2-(2-indanyl)ethoxy]-4-methoxybenzaldehyde

According to the same procedure as used in Example 4(1), using 2-(2-indanyl)ethanol instead of phenethyl alcohol, 3-[2-(2-indanyl)ethoxy]-4-methoxybenzaldehyde(yield 75.4%) was obtained as a colorless solid.

$^1$H-NMR (400 MHz, CDCl$_3$) δ 2.10 (2H, q, J=6.84 Hz), 2.66–2.72 (3H, m), 3.09–3.16 (2H, m), 3.95 (3H, s), 4.17 (2H, t, J=6.84 Hz), 6.98 (1H, d, J=8.30 Hz), 7.11–7.15 (2H, m), 7.18–7.21 (2H, m), 7.43 (1H, d, J=1.95 Hz), 7.46 (1H, dd, J=8.30, 1.95 Hz), 9.86 (1H, s).

(2) 2-amino-1-[3-[2-(2-indanyl)ethoxy]-4-methoxyphenyl]ethanol

According to the same procedure as used in Example 1(1), using 3-[2-(2-indanyl)ethoxy]-4-methoxybenzaldehyde instead of 3,4-dimethoxybenzaldehyde, 2-amino-1-[3-[2-(2-indanyl)ethoxy]-4-methoxyphenyl]ethanol was obtained as a brown oil.

$^1$H-NMR (400 MHz, CDCl$_3$) δ 2.05–2.10 (2H, m), 2.65–2.74 (3H, m), 2.81 (1H, dd, J=12.70, 7.81 Hz), 2.98 (1H, dd, J=12.70, 3.91 Hz), 3.08–3.15 (2H, m), 3.85 (3H, s), 4.11 (2H, t, J=6.84 Hz), 4.57 (1H, dd, J=7.81, 3, 91 Hz), 6.84 (1H, d, J=8.30 Hz), 6.88 (1H, dd, J=8.30, 1.47 Hz), 6.95 (1H, d, J=1.47 Hz), 7.10–7.15 (2H, m), 7.17–7.20 (2H, m).

(3) 2-[3-[2-(2-indanyl)ethoxy]-4-methoxyphenyl]morpholin-5-one

According to the same procedure as used in Example 3(2), using 2-amino-1-[3-[2-(2-indanyl)ethoxy]-4-methoxyphenyl]ethanol instead of 2-amino-1-(3-benzyloxy-4-methoxyphenyl)ethanol, the above-described compound (yield 64.6%) was obtained as a colorless solid.

$^1$H-NMR (400 MHz, CDCl$_3$) δ 2.08 (2H, q, J=6.84 Hz), 2.66–2.73 (3H, m), 3.09–3.16 (2H, m), 3.48 (1H, ddd, J=12.21, 3.42, 3.42 Hz), 3.57 (1H, dd, J=12.21, 10.26 Hz), 3.86 (3H, s), 4.12 (2H, t, J=6.84 Hz), 4.35 (1H, d, J=16.60 Hz), 4.45 (1H, d, J=16.60 Hz), 4.71 (1H, dd, J=10.26, 3.42 Hz), 6.11 (1H, broad), 6.87 (1H, d, J=8.30 Hz), 6.90 (1H, dd, J=8.30, 1.47 Hz), 6.96 (1H, d, J=1.47 Hz), 7.12–7.15 (2H, m), 7.17–7.22 (2H, m).

Example 51

Synthesis of 2-[3-[2-(2-indanyl)ethoxy]-4-methoxyphenyl]-4-methylmorpholin-5-one (Compound No. 51 of Table 1)

According to the same procedure as used in Example 12, using the 2-[3-[2-(2-indanyl)ethoxy]-4-methoxyphenyl] morpholin-5-one produced in Example 50 instead of 2-(3,4-dimethoxyphenyl)morpholin-5-one, the above-described compound (yield 81.9%) was obtained as a light brown oil.

$^1$H-NMR (400 MHz, CDCl$_3$) δ 2.06–2.11 (2H, m), 2.66–2.73 (3H, m), 3.02 (3H, s), 3.09–3.15 (2H, m), 3.33 (1H, dd, J=12.21, 2.93 Hz), 3.57 (1H, dd, J=12.21, 10.74 Hz), 3.86 (3H, s), 4.12 (2H, t, J=6.84 Hz), 4.32 (1H, d, J=16.60 Hz), 4.42 (1H, d, J=16.60 Hz), 4.76 (1H, dd, J=10.74, 2.93 Hz), 6.86 (1H, d, J=8.30 Hz), 6.90 (1H, dd, J=8.30, 1.95 Hz), 6.96 (1H, d, J=1.95 Hz), 7.11–7.15 (2H, m), 7.16–7.22 (2H, m).

Example 52

Synthesis of 2-(3-cyclopropylmethoxy-4-methoxyphenyl)-4-methylmorpholin-5-one (Compound No. 52 of Table 1)

According to the same procedure as used in Example 12, using the 2-(3-cyclopropylmethoxy-4-methoxyphenyl) morpholin-5-one produced in Example 8 instead of 2-(3,4-dimethoxyphenyl)morpholin-5-one, the above-described compound (yield 76.2%) was obtained as a yellow oil.

$^1$H-NMR (400 MHz, CDCl$_3$ ) δ 0.34–0.38 (2H, m), 0.63–0.68 (2H, m), 1.31–1.38 (1H, m), 3.02 (3H, s), 3.32 (1H, dd, J=12.69, 3.42 Hz), 3.55 (1H, dd, J=12.69, 10.74 Hz), 3.87 (2H, d, J=7.81 Hz), 3.88 (3H, s), 4.30 (1H, d, J=16.60 Hz), 4.41 (1H, d, J=16.60 Hz), 4.74 (1H, dd, J=10.74, 3.42 Hz), 6.86 (1H, d, J=8.30 Hz), 6.89 (1H, dd, J=8.30, 1.95 Hz), 6.93 (1H, d, J=1.95 Hz).

TABLE 1
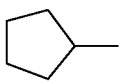
| Compound No. | R₁ | R₂ | R₃ | R₄ | R₅ | R₆ |
|---|---|---|---|---|---|---|
| 1 | Me | Me | H | H | H | H |
| 2 | 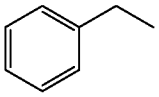 | Me | H | H | H | H |
| 3 | 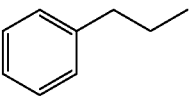 | Me | H | H | H | H |
| 4 | 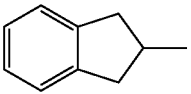 | Me | H | H | H | H |
| 5 | Bu | Me | H | H | H | H |
| 6 | 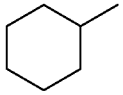 | Me | H | H | H | H |
| 7 |  | Me | H | H | H | H |
| 8 | 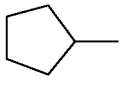 | Me | H | H | H | H |
| 9 | Me | Me | H | Me | H | H |
| 10 | 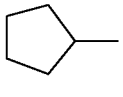 | Me | H | Me | H | H |
| 11 | 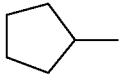 | Me | H | Ph | H | H |
| 12 | Me | Me | Me | H | H | H |
| 13 | 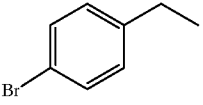 | Me | 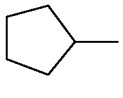 | H | H | H |
| 14 |  | Me | Me | H | H | H |

TABLE 1-continued
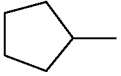
| Compound No. | R₁ | R₂ | R₃ | R₄ | R₅ | R₆ |
|---|---|---|---|---|---|---|
| 15 | 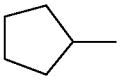 | Me | EtCO₂CH₂ | H | H | H |
| 16 | 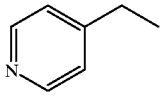 | Me | 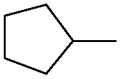 | H | H | H |
| 17 |  | Me | Et | H | H | H |
| 18 | 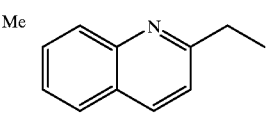 | Me | 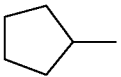 | H | H | H |
| 19 | 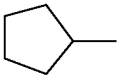 | Me | Bu | H | H | H |
| 20 |  | Me | 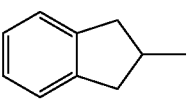 | H | H | H |
| 21 | 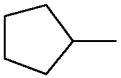 | Me | Me | H | H | H |
| 22 | 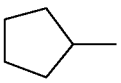 | Me | Me | Ph | H | H |
| 23 | 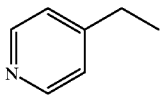 | Me | 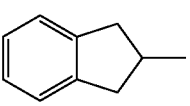 | Ph | H | H |
| 24 | 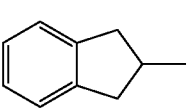 | Me | H | Ph | H | H |
| 25 |  | Me | Me | Ph | H | H |

TABLE 1-continued

| Compound No. | R₁ | R₂ | R₃ | R₄ | R₅ | R₆ |
|---|---|---|---|---|---|---|
| 26 | phenylpentyl | Me | H | H | H | H |
| 27 | 2-methylindanyl | Me | H | Me | H | H |
| 28 | 2-methylindanyl | Me | Me | Me | H | H |
| 29 | phenylhexyl | Me | Me | H | H | H |
| 30 | benzyloxypropyl | Me | H | H | H | H |
| 31 | cyclopentylmethyl | Me | H | H | Me | Me |
| 32 | 4-fluorophenylpropyl | Me | H | H | H | H |
| 33 | trans-4-phenylcyclohexylmethyl | Me | H | H | H | H |
| 34 | 1-phenylcyclopropylethyl | Me | H | H | H | H |
| 35 | 1-methyl-1-ethylcyclopropyl | Me | H | H | H | H |

TABLE 1-continued
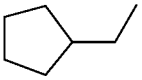
| Compound No. | R₁ | R₂ | R₃ | R₄ | R₅ | R₆ |
|---|---|---|---|---|---|---|
| 36 | 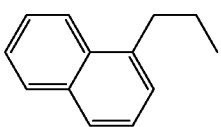 | Me | H | H | H | H |
| 37 | 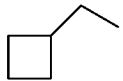 | Me | H | H | H | H |
| 38 | 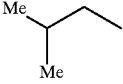 | Me | H | H | H | H |
| 39 | 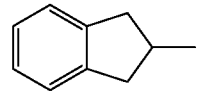 | Me | H | H | H | H |
| 40 | 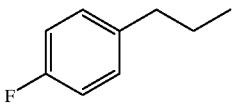 | Me | CH₃CH₂ | H | H | H |
| 41 | 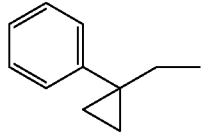 | Me | Me | H | H | H |
| 42 | 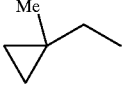 | Me | Me | H | H | H |
| 43 | 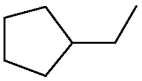 | Me | Me | H | H | H |
| 44 | 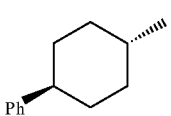 | Me | Me | H | H | H |
| 45 |  | Me | Me | H | H | H |

TABLE 1-continued

[Structure: morpholinone core with R1O, R2O on phenyl ring, R3 on N, R4 on C, R5 and R6 on C adjacent to O]

| Compound No. | R₁ | R₂ | R₃ | R₄ | R₅ | R₆ |
|---|---|---|---|---|---|---|
| 46 | benzyloxypropyl (PhCH₂-O-CH₂CH₂CH₂-) | Me | Me | H | H | H |
| 47 | 2-(naphthalen-1-yl)ethyl | Me | Me | H | H | H |
| 48 | cyclobutylmethyl | Me | Me | H | H | H |
| 49 | isobutyl (Me₂CHCH₂-... with Me, Me) | Me | Me | H | H | H |
| 50 | 2-(2,3-dihydro-1H-inden-2-yl)ethyl | Me | H | H | H | H |
| 51 | 2-(2,3-dihydro-1H-inden-2-yl)ethyl | Me | Me | H | H | H |
| 52 | cyclopropylmethyl | Me | Me | H | H | H |

Example 53

Production of Tablets 30 g of 2-(3-cyclopentyloxy-4-methoxyphenyl) morpholin-5-one (i.e., Compound No. 2 of Table 1), 253 g of lactose, 63 g of corn starch, 40 g of low-degree substituted hydroxypropylcellulose, and 4 g of calcium stearate were mixed together, then compressed by an ordinary method so that each tablet contained 10 mg of the above compound.

Example 54

Production of Capsules 30 g of 2-(3-butoxy-4-methoxyphenyl)morpholin-5-one (i.e., Compound No. 5 of Table 1), 260 g of lactose, 66 g of corn starch, and 4 g of calcium stearate were mixed together, then were filled into a gelatin capsule by an ordinary method so that each capsule contained 10 mg of the above compound.

Example 55

Production of Inhalant 0.15 g of 2-(3-cyclopentyloxy-4-methoxyphenyl)-4-methylmorpholin-5-one (i.e., Compound No. 14 of Table 1) pulverized well to a particle size of 1 to 5 μm and 60 g of lactose (325 mesh, DMV Co.) were mixed together. This was filled in capsules by an ordinary method so that each capsule contained 50 μg of the compound. Inhalation was performed by charging a capsule in a powder inhalation container.

Test Example 1

Separation of Phosphodiesterase (PDE) and Measurement of PDE Inhibitory Activity Type I, III, IV, and V PDE isozymes were prepared to study the PDE inhibitory activities of and selectivities with the compound of the invention [Trends Pharmacol Sci., 12, 19–27 (1992)]. Type I PDE was purchased from Sigma Corp. Type III, IV, and V PDE isozymes were partially purified from platelets (Type III and V) or neutrophils (Type IV) collected from rats. Each enzyme source was homogenized in a buffer (pH 6.5) containing 20 mM bisTris, 2 mM EDTA (i.e., ethylenediamine tetraacetate), 0.1 mM PMSF (i.e., phenylmethylsulfonyl fluoride), 5 mM 2-mercaptoethanol, 0.001 mM pepstatin and 0.01 mM leupeptin and was centrifuged at 30000×G for 30 minutes to obtain a supernatant, which was applied to an ion exchange column (Q-sepharose First Flow, Pharmacia Corp.) and was eluted with 0 to 1M sodium acetate. Partially purified isozymes were identified by observing the effects by conventional inhibitors.

Each PDE isozyme and the test compound dissolved in DMSO (i.e., dimethyl sulfoxide) were added to 50 mM Tris-HCl buffer containing 5 mM magnesium chloride. $^3$H-cAMP (for type III and IV PDE) or $^3$H-cGMP (for type I and V PDE) were added as substrates and were reacted at 30° C. for 30 minutes. The reaction was terminated by placing the test tube in boiling water of 100° C. for 5 minutes. The nucleotides formed by PDE were broken down by 5'-nucleotidase to $^3$H-adenosine or 3H-guanosine. The unreacted substrate and reaction product were separated through an ion-exchange column (i.e., QAE sephadex, Pharmacia Corp.) The eluted $^3$H-nucleoside was measured for its radioactivity by a liquid scintillation counter. The inhibitory activities of the compound of the present invention are shown by the $IC_{50}$ value (M). The inhibitory activities against Type IV is shown in Table 2. Further, the inhibitory activities of the test samples against Type I, III, and V are $\frac{1}{10}$ or less than that against type IV.

TABLE 2

| Compound No. | Type IV PDE inhibitory activity $IC_{50}$ (M) |
| --- | --- |
| 1 | $3.7 \times 10^{-5}$ |
| 2 | $1.5 \times 10^{-6}$ |
| 3 | $2.8 \times 10^{-5}$ |
| 4 | $2.7 \times 10^{-6}$ |
| 5 | $1.2 \times 10^{-5}$ |
| 6 | $3.2 \times 10^{-7}$ |
| 7 | $1.1 \times 10^{-5}$ |
| 8 | $2.5 \times 10^{-6}$ |
| 9 | $1.6 \times 10^{-5}$ |
| 10 | $3.0 \times 10^{-6}$ |
| 11 | $7.4 \times 10^{-8}$ |
| 12 | $4.7 \times 10^{-6}$ |
| 13 | $1.8 \times 10^{-6}$ |
| 14 | $3.1 \times 10^{-7}$ |
| 15 | $7.9 \times 10^{-6}$ |
| 16 | $5.5 \times 10^{-6}$ |
| 17 | $7.1 \times 10^{-7}$ |
| 18 | $4.5 \times 10^{-7}$ |
| 19 | $5.9 \times 10^{-6}$ |
| 20 | $2.0 \times 10^{-6}$ |
| 21 | $4.4 \times 10^{-8}$ |
| 22 | $2.5 \times 10^{-7}$ |
| 23 | $2.4 \times 10^{-6}$ |
| 24 | $3.0 \times 10^{-8}$ |
| 25 | $1.1 \times 10^{-7}$ |
| 26 | $6.2 \times 10^{-7}$ |
| 27 | $1.3 \times 10^{-7}$ |
| 28 | $3.0 \times 10^{-8}$ |
| 29 | $4.8 \times 10^{-7}$ |
| 30 | $5.7 \times 10^{-6}$ |
| 32 | $1.7 \times 10^{-6}$ |
| 33 | $7.2 \times 10^{-6}$ |
| 34 | $1.9 \times 10^{-6}$ |
| 35 | $1.3 \times 10^{-6}$ |
| 36 | $6.9 \times 10^{-6}$ |
| 37 | $2.7 \times 10^{-6}$ |
| 38 | $4.6 \times 10^{-6}$ |
| 39 | $7.8 \times 10^{-6}$ |
| 40 | $9.3 \times 10^{-8}$ |
| 41 | $3.8 \times 10^{-7}$ |
| 42 | $3.1 \times 10^{-7}$ |
| 43 | $6.1 \times 10^{-7}$ |
| 44 | $7.7 \times 10^{-7}$ |
| 45 | $5.8 \times 10^{-7}$ |
| 46 | $5.7 \times 10^{-7}$ |
| 47 | $3.0 \times 10^{-7}$ |
| 48 | $3.8 \times 10^{-7}$ |
| 49 | $3.5 \times 10^{-7}$ |
| 50 | $3.8 \times 10^{-6}$ |
| 51 | $1.0 \times 10^{-7}$ |
| 52 | $2.8 \times 10^{-6}$ |

Test Example 2

Inhibitory effects on activity of rat neutrophils

The release of super oxide anions was measured so as to study the inhibitory effects of the compound of the present invention on inflammatory leukocytes, that is, neutrophils.

Blood sample was collected from Wister rats anesthetized with ether. It was superposed on a blood cell separation solution (Polymorphoprep 1.113, made by Naicomed Farm), and the neutrophils were separated by centrifugation. The neutrophils were resuspended in a Hank's balanced salt solution at a concentration of $0.5 \times 10^4$ cells/ml 0.1 mM of Lusigenin and the test substance dissolved in DMSO were added to 2 ml of the cell-suspension. The chemiluminescence generated by stimulation of 0.3 $\mu$M calcium ionophore A23187 was measured by a chemiluminescence reader so as to evaluate the release of super oxide anions. The efficacy of the compounds of the present invention was expressed by an $IC_{50}$ value and is shown in Table 3.

TABLE 3

| Compound No. | Inhibitory action of super oxide anion release from rat neutrophils $IC_{50}$ (M) |
| --- | --- |
| 1 | $2.9 \times 10^{-5}$ |
| 2 | $5.8 \times 10^{-6}$ |
| 9 | $1.6 \times 10^{-6}$ |
| 13 | $1.4 \times 10^{-6}$ |

Test Example 3

Inhibitory effect on Antigen-Induced Bronchospasm (Anti-Asthmatic action)

A Hartley male guinea pig was sensitized by intramuscular administration of 35 mg Ovalbumin (OA) on first day and fourth day. A tracheal canula was introduced in the guinea pig anesthetized with pentobarbital and artificial ventilation was performed 25 to 29 days after the first sensitization. The overflow of the ventilation was measured by the Konzett-Roessler method while 0.2 mg/kg OA were administered intravenously. The test compound was dissolved in polyethylene glycol 400 and intravenously administered 10 minutes before administration of the antigens. The effect of the present invention was expressed by the $ED_{50}$ value and is shown in Table 4.

TABLE 4

| Compound No. | Action for suppressing antigen-induced bronchospasms $ED_{50}$ (mg/kg) |
| --- | --- |
| 2 | 0.48 |
| 5 | 3.6 |
| 8 | 4.31 |
| 14 | 2.1 |
| 27 | 7.99 |
| 35 | 6.22 |
| 36 | 1.00 |
| 38 | 7.83 |
| 39 | 8.04 |

Test Example 4

Acute Toxicity Test

Compound of the present invention of Nos. 1 to 52 of Table 1 were suspended in a saline containing 0.5% sodium carboxylmethylcellulose and were administered ddY male mouse intraperitoneally. The survival rate of the next day was examined. No death was observed at a dosage of 30 mg/kg of any compound.

Industrial Applicability

As described above, the compound according to the present invention exhibits an excellent type IV PDE inhibitory activity and is very useful for treating inflammatory diseases such as asthma and dermatitis and autoimmune diseases such as multiple sclerosis and rheumatism.

What is claimed is:

1. A method for preventing or treating inflammatory diseases comprising administrating to a person in need thereof a 2-phenylmorpholin-5-one derivative having the formula (I):

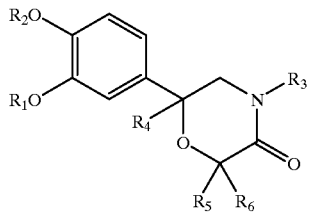

(I)

wherein $R_1$ represents a substituted or unsubstituted $C_1$ to $C_8$ allyl group; a substituted or unsubstituted $C_3$ to $C_7$ cycloalkyl group; or indanyl group, $R_2$ represents a $C_1$ to $C_4$ alkyl group, $R_3$ represents a hydrogen atom; a substituted or unsubstituted $C_1$ to $C_5$ alkyl group; a substituted or unsubstituted $C_3$ to $C_7$ cycloalkyl group; a substituted or unsubstituted aryl group which may include at least one hetero atom selected from the group consisting of an oxygen atom, a nitrogen atom and a sulfur atom; or an acyl group, $R_4$ represents a hydrogen atom; a substituted or unsubstituted $C_1$ to $C_6$ alkyl group; or a substituted or unsubstituted aryl group which may include at least one hetero atom selected from the group consisting of an oxygen atom, a nitrogen atom and a sulfur atom, $R_5$ and $R_6$ each independently represent a hydrogen atom; a substituted or unsubstituted $C_1$ to $C_5$ alkyl group; a substituted or unsubstituted $C_3$ to $C_7$ cycloalkyl group; or a substituted or unsubstituted aryl group which may include at least one hetero atom selected from the group consisting of an oxygen atom, a nitrogen atom and a sulfur atom, an optical isomer thereof, or a pharmacologically acceptable salt thereof, or a hydrate or solvate thereof and a pharmacologically acceptable carrier.

2. A method according to claim 1 wherein $R_1$ is a $C_1$ to $C_6$ alkyl group; $C_1$ to $C_5$ alkyl group having, as a substituent, at least one group selected from the group consisting of a substituted or unsubstituted aryl group, a substituted or unsubstituted alkoxy group and a substituted or unsubstituted $C_3$ to $C_7$ cycloalkyl group; a substituted or unsubstituted $C_4$ to $C_6$ cycloalkyl group; or indanyl group.

3. A method according to claim 1 wherein $R_1$ is a methyl group, an n-butyl group; a 2-methylpropyl group; a cyclopropylmethyl group; a cyclobutylmethyl group; a cyclopentylmethyl group; a $C_1$ to $C_5$ alkyl group having, as a substituent, a phenyl group, a naphthyl group, abenzyloxy group, a 4-fluorophenyl group, a phenylcyclopropyl group, a methylcyclopropyl group, or an indanyl group; a cyclopentyl group; a cyclohexyl group; a 4-phenylcyclohexyl group; or a 2-indanyl group.

4. A method according to claim 1 wherein $R_2$ is a methyl group.

5. A method according to claim 1 wherein $R_3$ is a hydrogen atom, a $C_1$ to $C_4$ alkyl group; a $C_1$ to $C_3$ alkyl group substituted with an aryl group which may be substituted with a halogen atom and may include at least one hetero atom selected from the group consisting of an oxygen atom, a nitrogen atom and a sulfur atom or with an ethoxycarbonyl group; or an acetyl group.

6. A method according to claim 1 wherein $R_4$ is a hydrogen atom, a $C_1$ to $C_3$ alkyl group or a phenyl group.

7. A method according to claim 1 wherein $R_5$ and $R_6$ are hydrogen atoms.

8. A method for treating asthma comprising administrating to a person in need thereof a 2-phenylmorpholin-5-one derivative having the formula (I):

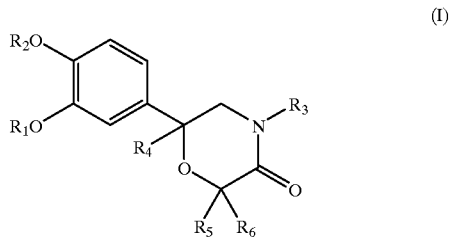

(I)

wherein $R_1$ represents a substituted or unsubstituted $C_1$ to $C_8$ alkyl group; a substituted or unsubstituted $C_3$ to $C_7$ cycloalkyl group; or indanyl group, $R_2$ represents a $C_1$ to $C_4$ alkyl group $R_3$ represents a hydrogen atom; a substituted or unsubstituted $C_1$ to $C_5$ alkyl group; a substituted or unsubstituted $C_3$ to $C_7$ cycloalkyl group; a substituted or unsubstituted aryl group which may include at least one hetero atom selected from the group consisting of an oxygen atom, a nitrogen atom and a sulfur atom; or an acyl group, $R_4$ represents a hydrogen atom, a substituted or unsubstituted $C_1$ to $C_6$ alkyl group; or a substituted or unsubstituted aryl group which may include at least one hetero atom selected from the group consisting of an oxygen atom, a nitrogen atom and a sulfur atom, $R_5$ and $R_6$ each independently represent a hydrogen atom; a substituted or unsubstituted $C_1$ to $C_5$ alkyl group; a substituted or unsubstituted $C_3$ to $C_7$ cycloalkyl group; or a substituted or unsubstituted aryl group which may include at least one hetero atom selected from the group consisting of an oxygen atom, a nitrogen atom and a sulfur atom, an optical isomer thereof, or a pharmacologically acceptable salt thereof, or a hydrate or solvate thereof and a pharmacologically acceptable carrier.

9. A method according to claim 8 wherein $R_1$ is a $C_1$ to $C_6$ alkyl group; $C_1$ to $C_5$ alkyl group having, as a substituent, at least one group selected from the group consisting of a substituted or unsubstituted aryl group, a substituted or unsubstituted alkoxy group and a substituted or unsubstituted $C_3$ to $C_7$ cycloalkyl group; a substituted or unsubstituted $C_4$ to $C_6$ cycloalkyl group; or indanyl group.

10. A method according to claim 8 wherein $R_1$ is a methyl group, an n-butyl group; a 2-methylpropyl group; a cyclopropylmethyl group; a cyclobutylmethyl group; a cyclopentylmethyl group; a $C_1$ to $C_5$ alkyl group having, as a substituent, a phenyl group, a naphthyl group, a benzyloxy group, a 4-fluorophenyl group, a phenylcyclopropyl group, a methylcyclopropyl group, or an indanyl group; a cyclopentyl group; a cyclohexyl group; a 4-phenylcyclohexyl group; or a 2-indanyl group.

11. A method according to claim 8 wherein $R_2$ is a methyl group.

12. A method according to claim 8 wherein $R_3$ is a hydrogen atom, a $C_1$ to $C_4$ alkyl group; a $C_1$ to $C_3$ alkyl group substituted with an aryl group which may be substituted with a halogen atom and may include at least one hetero atom selected from the group consisting of an oxygen atom, a nitrogen atom and a sulfur atom or with an ethoxycarbonyl group; or an acetyl group.

13. A method according to claim 8 wherein $R_4$ is a hydrogen atom, a $C_1$ to $C_3$ alkyl group or a phenyl group.

14. A method according to claim 8 wherein $R_5$ and $R_6$ are hydrogen atoms.

* * * * *

UNITED STATES PATENT AND TRADEMARK OFFICE
CERTIFICATE OF CORRECTION

PATENT NO.    : 6,265,402 B1
DATED         : July 24, 2001
INVENTOR(S)   : Shinji Ina, Kenjirou Yamana and Kyoji Noda It is certified that error appears in the above-identified patent and that said Letters Patent is hereby corrected as shown below:

<u>Column 43,</u>
Line 46, replace "allyl" with -- alkyl --.

Signed and Sealed this

Third Day of December, 2002

JAMES E. ROGAN
*Director of the United States Patent and Trademark Office*